United States Patent
Skrzypczynski et al.

(10) Patent No.: US 7,462,451 B2
(45) Date of Patent: Dec. 9, 2008

(54) COMPOSITIONS FOR MODIFYING NUCLEIC ACIDS

(75) Inventors: Zbigniev Skrzypczynski, Verona, WI (US); Sarah R. Wayland, Madison, WI (US)

(73) Assignee: Third Wave Technologies, Inc., Madison, WI (US)

(*) Notice: Subject to any disclaimer, the term of this patent is extended or adjusted under 35 U.S.C. 154(b) by 0 days.

(21) Appl. No.: 11/114,288

(22) Filed: Apr. 26, 2005

(65) Prior Publication Data

US 2005/0277138 A1   Dec. 15, 2005

Related U.S. Application Data

(60) Provisional application No. 60/565,295, filed on Apr. 26, 2004.

(51) Int. Cl.
- C12Q 1/68 (2006.01)
- C07H 21/02 (2006.01)
- C07C 233/18 (2006.01)

(52) U.S. Cl. .................... 435/6; 530/409; 564/123
(58) Field of Classification Search ............ 564/123; 435/6; 530/409

See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,965,188 A | 10/1990 | Mullis et al. |
| 5,011,769 A | 4/1991 | Duck et al. |
| 5,124,246 A | 6/1992 | Urdea et al. |
| 5,288,609 A | 2/1994 | Engelhardt et al. |
| 5,403,711 A | 4/1995 | Walder et al. |
| 5,409,818 A | 4/1995 | Davey et al. |
| 5,432,272 A | 7/1995 | Benner |
| 5,474,796 A | 12/1995 | Brennan |
| 5,538,848 A | 7/1996 | Livak et al. |
| 5,624,802 A | 4/1997 | Urdea et al. |
| 5,660,988 A | 8/1997 | Duck et al. |
| 5,710,264 A | 1/1998 | Urdea et al. |
| 5,792,614 A | 8/1998 | Western et al. |
| 5,846,717 A | 12/1998 | Brow et al. |
| 5,849,481 A | 12/1998 | Urdea et al. |
| 5,851,770 A | 12/1998 | Babon et al. |
| 5,858,659 A | 1/1999 | Sapolsky et al. |
| 5,882,867 A | 3/1999 | Ullman et al. |
| 5,912,340 A | 6/1999 | Kutyavin et al. |
| 5,914,230 A | 6/1999 | Liu et al. |
| 5,919,626 A | 7/1999 | Shi et al. |
| 5,925,525 A | 7/1999 | Fodor et al. |
| 5,952,174 A | 9/1999 | Nikiforov et al. |
| 5,958,692 A | 9/1999 | Cotton et al. |
| 5,985,551 A | 11/1999 | Brennan |
| 5,985,557 A | 11/1999 | Prudent et al. |
| 5,994,069 A | 11/1999 | Hall et al. |
| 6,001,311 A | 12/1999 | Brennan |
| 6,001,567 A | 12/1999 | Brow et al. |
| 6,001,983 A | 12/1999 | Benner |
| 6,013,170 A | 1/2000 | Meade |
| 6,017,696 A | 1/2000 | Heller |
| 6,037,120 A | 3/2000 | Benner |
| 6,045,996 A | 4/2000 | Cronin et al. |
| 6,051,380 A | 4/2000 | Sosnowski et al. |
| 6,063,573 A | 5/2000 | Kayyem |
| 6,068,818 A | 5/2000 | Ackley et al. |
| 6,090,543 A | 7/2000 | Prudent et al. |
| 6,110,677 A | 8/2000 | Western et al. |
| 6,110,684 A | 8/2000 | Kemper et al. |
| 6,121,001 A | 9/2000 | Western et al. |
| 6,127,121 A | 10/2000 | Meyer, Jr. et al. |
| 6,140,496 A | 10/2000 | Benner |
| 6,143,877 A | 11/2000 | Meyer et al. |
| 6,150,097 A | 11/2000 | Tyagi et al. |
| 6,183,960 B1 | 2/2001 | Lizardi |
| 6,210,884 B1 | 4/2001 | Lizardi et al. |
| 6,221,583 B1 | 4/2001 | Kayyem et al. |
| 6,248,229 B1 | 6/2001 | Meade |
| 6,348,314 B1 | 2/2002 | Prudent et al. |
| 6,458,535 B1 | 10/2002 | Hall et al. |

FOREIGN PATENT DOCUMENTS

| | | |
|---|---|---|
| WO | WO 97/27214 | 7/1997 |
| WO | WO 98/42873 | 10/1998 |
| WO | WO 99/67641 | 12/1999 |
| WO | WO 00/39587 | 7/2000 |

OTHER PUBLICATIONS

Letsinger and Lunsdorf, "Synthesis of thymidine oligonucleotides by phosphite triester intermediates," (1976) J. Am. Chem. Soc. 98:3655-3661.

(Continued)

*Primary Examiner*—Golam M. M. Shameem
*Assistant Examiner*—Joseph R Kosack
(74) *Attorney, Agent, or Firm*—Casimir Jones, S.C.

(57) ABSTRACT

The present invention relates to compositions and methods for the preparation of modified nucleic acids. In particular, the present invention provides novel reagents and chemistries for the generation of linkers, modified phosphoramidites, and modified solid supports.

2 Claims, 12 Drawing Sheets

OTHER PUBLICATIONS

Beaucage and Iyer, "Advances in the Synthesis of Oligonucleotides by the Phosphoramidite Approach," (1992) Tetrahedron, 48: 2223-2311.

Matray et al., "Synthesis of oligonucleotides containing 3'-alkylcarboxylic acids using a palladium labile oligonucleotide solid phase synthesis support," (1997) Bioconjugate Chem 8:99-102.

Lyttle et al., "Versatile linker chemistry for synthesis of 3'-modified DNA," (1997) Bioconjugate Chem. 8:193-198.

Agrawal and Iyer, Modified oligonucleotides as therapeutic and diagnostic agents, (1995) Curr. Opin. Biotechnol. 6:12-19.

Zhao et al., "Immobilization of oligodeoxyribonucleotides with multiple anchors to microchips," (2001) Nucleic Acids Res. 29:955-959.

Barany, "Genetic Disease Detection and DNA Amplification Using Cloned Thermostable Ligase," Proc. Natl. Acad. Sci USA 88, 189-93 (1991).

Habus et al., "A Mild and Efficient Solid-Support Synthesis of Novel Oligonucleotide Conjugates," (1998) Bioconjugate Chem. 9: 283-291.

Stetsenko et al., "Genetic Disease Detection and DNA Amplification Using Cloned Thermostable Ligase ," (2001) Bioconjugate Chem. 12:576-586.

Marshall, "Tumor suppressor genes," Cell, 64: 313-326 (1991).

Hausch and Jäschke, "Multifuncational dinucleotide analogs for the generation of complex RNA conjugates," (2001) Tetrahedron Lett. 57, 1261-1268.

Walton et al., "Evaluation of new linkers and synthetic methods for internal modified oligonucleotides," (2002) Bioconjug Chem 13, 1155-1158.

Sojka et al., "A novel phosphoramidite method for automated synthesis of oligonucleotides on glass supports for biosensor development," (2000) Appl Biochem Biotechnol 89, 85-103.

Vogel et al., "A substituted triaza crown ether as a binding site in DNA conjugates," (2003) Chem Commun 21(8):1006-1007.

Wu, X., and Pitsch, S., "Synthesis and pairing properties of oligoribonucleotide analogues containing a metal-binding site attached to beta-D-allofuranosyl cytosine," (1998) Nucleic Acids Res 26, 4315-4323.

Niemeyer, "The developments of semisynthetic DNA-protein conjugates," 20:395-401(2002).

Guzaev et al., "A New Approach for Chemical Phosphorylation of Oligonucleotides at the 5'-Terminus," Tetrahedron 51:9375-9384 (1995).

Caruthers et al., (1987) Methods Enzymol. 154:287-313.

Guzayev et al., (1995) Tetrahedron 51, 9375-9384.
Matysiak et al., (1997) Nucleosides & Nucleotides 16:855-861.
Nielsen, et al. Anticancer Drug Des. 8:53 63 [1993].
Trevisiol et al., (2000) Nucleosides, Nucleotides & Nucleic Acids 19:1427-1439.
Krotz et al., (2001) Bioorg. Med.Chem. Lett. 11:1863-1867.
Defrancq and Lhomme, (2001) Biorg. Med. Chem. Lett. 11:931-3.
Asseline and Thuong (1997) New J. Chem. 21: 5-17.
Zatsepin et al., (2002) Bioconjugate Chem. 13(4):822-830.
Forget et al., (2001) Tetrahedron Lett. 42, 7829-7832.
Podyminogin et al., (2001) Nucleic Acids Res. 29:5090-5098.
Lindroos et al., (2001) Nucleic Acids Res. 29:e69.
Dombi et al., (2002) Synthesis 6: 816-824.
Tilquin et al., (2001) Bioconjugate Chem. 12:451-457.
Karino et al., (2001) Nucleic Acids Res. 29: 2456-2463.
Ruth, (1994) Methods in Molecular Biology 26, 167-185.
Salo et al., (1999) Bioconjugate Chem. 10:815-823.
Forget et al., (2001) Chem. Eur. J. 7: 3976-3984.
Weinberg, Science, 254: 1138-1146 (1991).
Lyamichev et al., Nat. Biotech., 17:292 (1999).
Hall et al., PNAS, USA, 97:8272 (2000).
Hovinen et al., (1993) Tetrahedron Lett. 34:5163-5166.
Montserat et al., (1993) Nucleotides, Nucleosides 12:967-971.
Allawi, H.T. & SantaLucia, J., Jr. Thermodynamics and NMR of internal G. T mismatches in DNA. Biochemistry 36, 10581-94 (1997).
Pon and Yu (1997) Nucleic Acids Res. 25: 3629-363.
Greenberg and Kahl (2001) J.Org.Chem. 66:7151-7154.
Czaplinski and Sheppard, (2001) J. Am. Chem. Soc. 123:8618-8619.
Watterson et al., (2000) Langmuir 16, 4984-4992.
Steel et al., (2000) Biophys. J. 79, 975-81.
Shchepinov et al., (1997) Nucleic Acids Res. 25, 1155-1161.
Jäschke et al., (1993) Tetrahedron Lett. 34, 301-304.
Greenwald et al., (2000) Crit. Rev. Ther. Drug Carrier Syst. 17, 101-61.
Bonora et al., (1997) Bioconjugate Chem. 8, 793-797.
Jäschke et al., (1994) Nucleic Acids Res. 22, 4810-4817.
Jäschke et al., (1996) Nucleosides, Nucleotides 15, 1519-1529.
Afanassiev et al., (2000) Nucleic Acid Res. 28, E66-e66.
Hermanson, G.T. (1996) Bioconjugate techniques. Academic Press, pp. 185-186.
Urata et al., (1993) Tetrahedron Lett. 34,4015-4018.
Horn et al., (1997) Nucleic Acids Res. 25, 4842-4849.
McBride et al., (1988) Biotechniques 6, 362-7.

15

16

A.

B.

(5') HO—CCA-TTT-TCA-G-O-P(O)$_2$O—L$_2$—O-P(O)$_2$O-AAT-TGG-GTG-T-O-P(O)$_2$O—L$_1$—OH (3')

17

C.

8e

R" = /\/\O/\/O\/\O/\/\NH-(O)C-DABCYL
R' = /\O/\

(5') HO-L₃-O-P(O)₂O-CCA-TTT-TCA-GAA-TTG-GGT-GT-OH (3')

23

COMPOSITIONS FOR MODIFYING NUCLEIC ACIDS

The present Application claims priority to U.S. Provisional Application Ser. No. 60/565,295, filed Apr. 26, 2004, herein incorporated by reference.

FIELD OF THE INVENTION

The present invention relates to compositions and methods for the preparation of modified nucleic acids. In particular, the present invention provides novel reagents and chemistries for the generation of linkers and modified phosphoramidites.

BACKGROUND

Modified oligonucleotides, DNA probes, and their conjugates are of great value in molecular biological research and in applications such as anti-viral therapy, as probes for detecting nucleic acids, as aids in molecular biology and as pharmaceuticals or diagnostic agents. Modified oligonucleotides that can block RNA translation and are nuclease resistant are useful as inhibitors of gene expression (e.g., antisense oligonucleotides, ribozymes, sense oligonucleotides and triplex-forming oligonucleotides). Oligonucleotides are important materials for research, diagnostic, therapeutic and other purposes. An ever-growing demand for improved oligonucleotides, oligonucleotide analogs and for methods for their preparation and use has arisen. Chemically modified DNA probes and their conjugates play increasingly sophisticated roles in the disparate areas of biotechnology (e.g., Barrett et al. (2003) *Drug Discov Today* 8, 134-141), medicine (e.g., Barrett et al., (2003) *Drug Discov Today* 8, 134-141), and nanotechnology (e.g., Agrawal et al., (1995) *Curr Opin Biotechnol* 6, 12-19). Recent chemical literature reports the synthesis of a variety of reagents and modified solid supports that allow modifications to be introduced into the structure of chemically synthesized oligonucleotides (Walton et al., (2002) *Bioconjug Chem* 13, 1155-1158); Niemeyer, (2002) *Trends Biotechnol* 20, 395-401; Ghosh et al., (2000) *J Ind Chem Soc* 77, 109-132). Among the many existing synthetic methods, the phosphoramidite approach is used most frequently in the synthesis of a wide variety of modified DNA probes (Sojka et al., (2000) *Appl Biochem Biotechnol* 89, 85-103). The discovery of the phosphoramidite method, which enables automated synthesis of natural and modified DNA molecules (Letsinger and Lunsdorf (1976) J. Am. Chem. Soc. 98:3655-3661; Caruthers et al., (1987) Methods Enzymol. 154:287-313; Beaucage and Iyer (1992) Tetrahedron, 48: 2223-2311; Protocols for Oligonucleotides and Analogs. Methods in Molecular Biology, Vol 20, Edited by Sudhir Agraval, Humana Press 1993), has stimulated the development of numerous reagents and methods to introduce a specific modification or functional group at a selected position within a synthesized oligonucleotide (Guzayev et al., (1995) Tetrahedron 51, 9375-9384; Matray et al., (1997) Bioconjugate Chem. 8:99-102; Lyttle et al., (1997) Bioconjugate Chem. 8:193-198). Some phosphoramidite labeling reagents are commercially available.

However, escalating interest in the use of chemically modified synthetic oligonucleotides in the disciplines of biology, medicine, and biotechnology (Agraval and Iyer (1999) Curr. Opin. Biotechnol. 6:12-19; Delivery Strategies for Antisense Oligonucleotide Therapeutics. Ed. Saghir Akhtar, CRC Press, 1995; Matysiak et al., (1997) Nucleosides & Nucleotides 16:855-861; Zhao et al., (2001) Nucleic Acids Res. 29:955-959) has intensified the need for less expensive and more broadly applicable labeling reagents. Despite popularity and efficiency, automated oligonucleotide synthesis cannot always address all synthetic requirements. Generally, phosphoramidite reagents used in the synthesis of modified DNA probes can be divided into two groups: A and B.

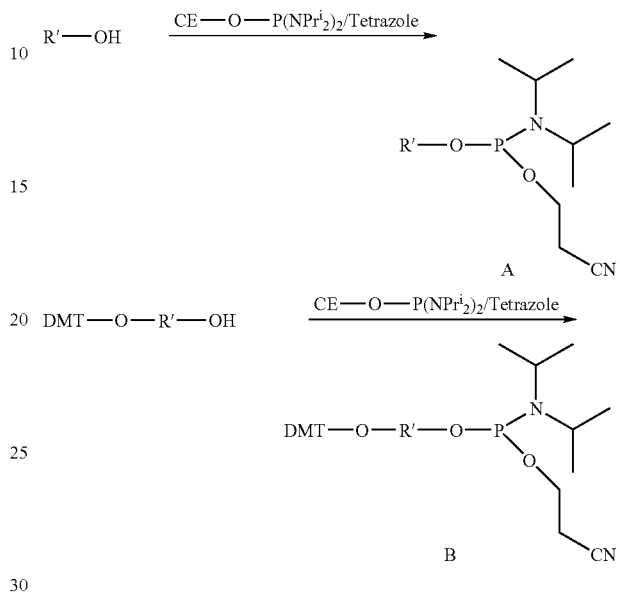

Group A phosphoramidites introduce a modification into the 5' loci of the synthesized oligonucleotide, and group B phosphoramidites introduce a modification into the 3' or 5' or internal loci of the synthesized DNA molecule.

Group A phosphoramidites can be prepared with the appropriate starting compound R' that has a hydroxyl group available for further transformations. All other functional groups of compound R' are blocked with protecting groups that are compatible with the phosphoramidite method of oligonucleotide synthesis. The synthesis of group B phosphoramidites, however, requires preparation of an intermediate material that contains two hydroxyl groups, one of which must be selectively protected with a DMT protecting group, and one that is kept available for the phosphitylation reaction. In consequence, the preparation of group B reagents requires more labor and time-consuming synthetic effort.

Increasingly, efforts have been focused on the development of new post-synthetic strategies for the preparation of oligonucleotide conjugates with other molecules and biological moieties, as well as on new protocols for immobilizing DNA onto solid surfaces. However, flexible, effective, and efficient methods of modifying and conjugating oligonucleotides are still needed.

SUMMARY OF THE INVENTION

The present invention relates to compositions and methods for the preparation of modified nucleic acids. In particular, the present invention provides novel reagents and chemistries for the generation of linkers and modified phosphoramidates.

Accordingly, in some embodiments, the present invention provides a composition comprising:

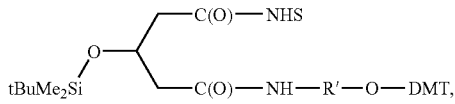

wherein tBuMe2Si refers to tert-butyldimethylsiloxy, NHS refers to N-hydroxysuccinimide, and DMT refers to dimethoxytrityl.

In some embodiments, R' is a linker (e.g., $CH_2CH_2$). In certain embodiments R' is selected from the group consisting of: amino groups, hydrazido groups, aminooxy groups, aldehyde groups, carboxyl groups, thiol groups, phosphorothioate groups, heteroatoms, organic moieties, ligands, variable length linkers, hydrazido, dyes, photochemically active groups, an organic molecule of generic structure $H_2N$—R—OH, fluorescent labels, chemiluminescent labels, enzymatically reactive labels, linkers and spacers.

Groups that could be used in place of tBuMe2Si (in any of the formulas described herein), include, but are not limited to: cyclic anhydrides (e.g. of carboxylic, thiocarboxylic, sulfonic, phosphoric, thiophosphoric, phosphonic, thiophosphonic, phosphinic and thiophosphinic acids) structure of which contains protected functional group (e.g. hydroxyl, amino, mercapto or other) which after deprotection can be used in further conjugation/immobilization steps or can be converted into another reactive organic moiety (e.g phosphoramidie) useful for the synthesis of modified DNA probes. Derivatives of the reactive cyclic anhydrides may also contain heteroatoms like selenium (e.g. selenophosphoric, phosphonic or phosphinic acids), nitrogen or other heteroatoms.

In other embodiments, the present invention provides a composition comprising

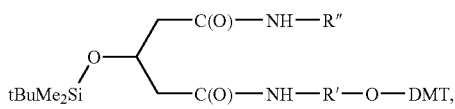

wherein tBuMe2Si refers to tert-butyldimethylsiloxy, and DMT refers to dimethoxytrityl.

In some embodiments, R' and R" comprise amino groups, hydroxy amines, hydrazido groups, aminooxy groups, aldehyde groups, carboxyl groups, thiol groups, phosphorothioate groups, heteroatoms, organic moieties, ligands, variable length linkers, hydrazido, dyes, photochemically active groups, or an organic molecule of generic structure $H_2N$—R—OH. In preferred embodiments, R' is $CH_2CH_2$. In other embodiments, R' is a variable length linker. In some embodiments, R' and R" are labels (e.g., including, but not limited to, fluorescent labels, chemiluminescent labels, and enzymatically reactive labels, linkers or spacers). In other embodiments, R" is a biological molecule (e.g., a protein, an antibody, a lipid, or a carbohydrate).

In still further embodiments, the present invention provides a composition comprising a modified solid support comprising the structure:

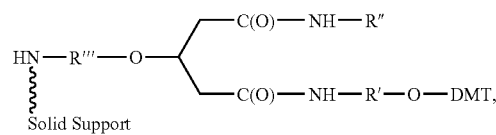

wherein DMT refers to dimethoxytrityl

In some embodiments, R''' is $CO(CH_2)_2CO$. In certain embodiments R''' is selected from the group consisting of: amino groups, hydrazido groups, aminooxy groups, aldehyde groups, carboxyl groups, thiol groups, phosphorothioate groups, heteroatoms, organic moieties, ligands, variable length linkers, hydrazido, dyes, photochemically active groups, an organic molecule of generic structure $H_2N$—R—OH, fluorescent labels, chemiluminescent labels, enzymatically reactive labels, linkers and spacers.

In some embodiments, the solid support is controlled pore glass. In some embodiments, R' and R" comprise amino groups, hydroxy amines, hydrazido groups, aminooxy groups, aldehyde groups, carboxyl groups, thiol groups, phosphorothioate groups, heteroatoms, organic moieties, ligands, variable length linkers, hydrazido, dyes, photochemically active groups, or an organic molecule of generic structure $H_2N$—R—OH. In preferred embodiments, R' is $CH_2CH_2$. In other embodiments, R' is a variable length linker. In some embodiments, R' and R" are labels (e.g., including, but not limited to, fluorescent labels, chemiluminescent labels, and enzymatically reactive labels, linkers or spacers). In other embodiments, R" is a biological molecule.

In yet other embodiments, the present invention provides a composition comprising a modified phosphoramidite comprising the structure:

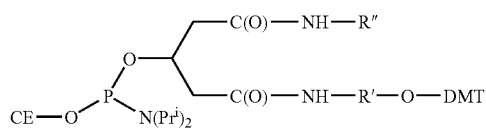

wherein CE refers to cyanoethyl and to and $Pr^i$ refers to isopropyl. In some embodiments, R' and R" comprise amino groups, hydroxy amines, hydrazido groups, aminooxy groups, aldehyde groups, carboxyl groups, thiol groups, phosphorothioate groups, heteroatoms, organic moieties, ligands, variable length linkers, hydrazido, dyes, photochemically active groups, or an organic molecule of generic structure $H_2N$—R—OH. In preferred embodiments, R' is $CH_2CH_2$. In other embodiments, R' is a variable length linker. In some embodiments, R' and R" are labels (e.g., including, but not limited to, fluorescent labels, chemiluminescent labels, and enzymatically reactive labels, linkers or spacers). In other embodiments, R" is a biological molecule (e.g., a protein, an antibody, a lipid, or a carbohydrate).

The present invention further provides a composition comprising a nucleic acid comprising the structure:

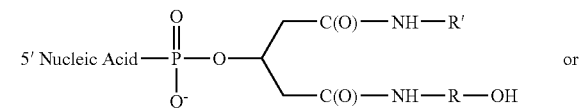

or

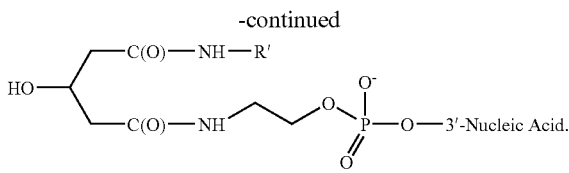

In some embodiments, R' is a label (e.g., including, but not limited to, fluorescent labels, chemiluminescent labels, or enzymatically reactive labels, linkers or spacers). In some embodiments, R' is a biological molecule (e.g., a protein, an antibody, a lipid, or a carbohydrate). In certain embodiments, R is $CH_2CH_2$.

The present invention additionally provides a method of labeling nucleic acids, comprising providing a nucleic acid labeling reagent comprising the structure:

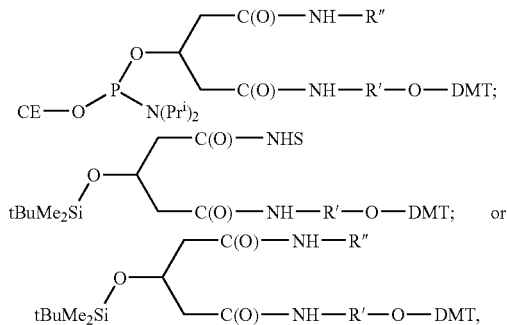

wherein tBuMe2Si refers to tert-butyldimethylsiloxy, NHS refers to N-hydroxysuccinimide, CE refers to cyanoethyl and to and $Pr^i$ refers to isopropyl, and DMT refers to dimethoxytrityl; and contacting the nucleic acid labeling reagent with a nucleic acid under conditions such that the nucleic acid labeling reagent is covalently linked to said nucleic acid. In some embodiments, the nucleic acid labeling reagent is attached to a solid support (e.g., CPG). In other embodiments, the nucleic acid labeling reagent is attached to a second nucleic acid. In certain embodiments, the nucleic acid labeling reagent is attached to a solid support. In some embodiments, the solid support comprises an array of nucleic acid labeling reagents. In some embodiments, the nucleic acid is an oligonucleotide. In some embodiments, R' and R" comprise amino groups, hydroxy amines, hydrazido groups, aminooxy groups, aldehyde groups, carboxyl groups, thiol groups, phosphorothioate groups, heteroatoms, organic moieties, ligands, variable length linkers, hydrazido, dyes, photochemically active groups, or an organic molecule of generic structure $H_2N$—R—OH. In preferred embodiments, R' is $CH_2CH_2$. In other embodiments, R' is a variable length linker. In some embodiments, R' and R" are labels (e.g., including, but not limited to, fluorescent labels, chemiluminescent labels, and enzymatically reactive labels, linkers or spacers). In other embodiments, R" is a biological molecule (e.g., a protein, an antibody, a lipid, or a carbohydrate).

The present invention also provides a kit comprising a nucleic acid labeling reagent comprising the structure:

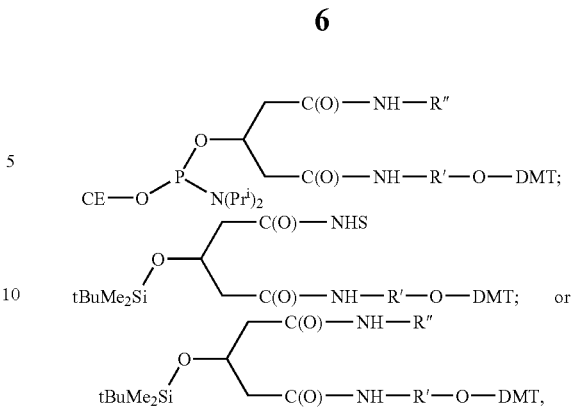

wherein tBuMe2Si refers to tert-butyldimethylsiloxy, NHS refers to N-hydroxysuccinimide, CE refers to cyanoethyl and to and $Pr^i$ refers to isopropyl and DMT refers to dimethoxytrityl. In some embodiments, R' and R" comprise amino groups, hydroxy amines, hydrazido groups, aminooxy groups, aldehyde groups, carboxyl groups, thiol groups, phosphorothioate groups, heteroatoms, organic moieties, ligands, variable length linkers, hydrazido, dyes, photochemically active groups, or an organic molecule of generic structure $H_2N$—R—OH. In preferred embodiments, R' is $CH_2CH_2$. In other embodiments, R' is a variable length linker. In some embodiments, R' and R" are labels (e.g., including, but not limited to, fluorescent labels, chemiluminescent labels, and enzymatically reactive labels, linkers or spacers). In other embodiments, R" is a biological molecule.

DEFINITIONS

Figure 1:
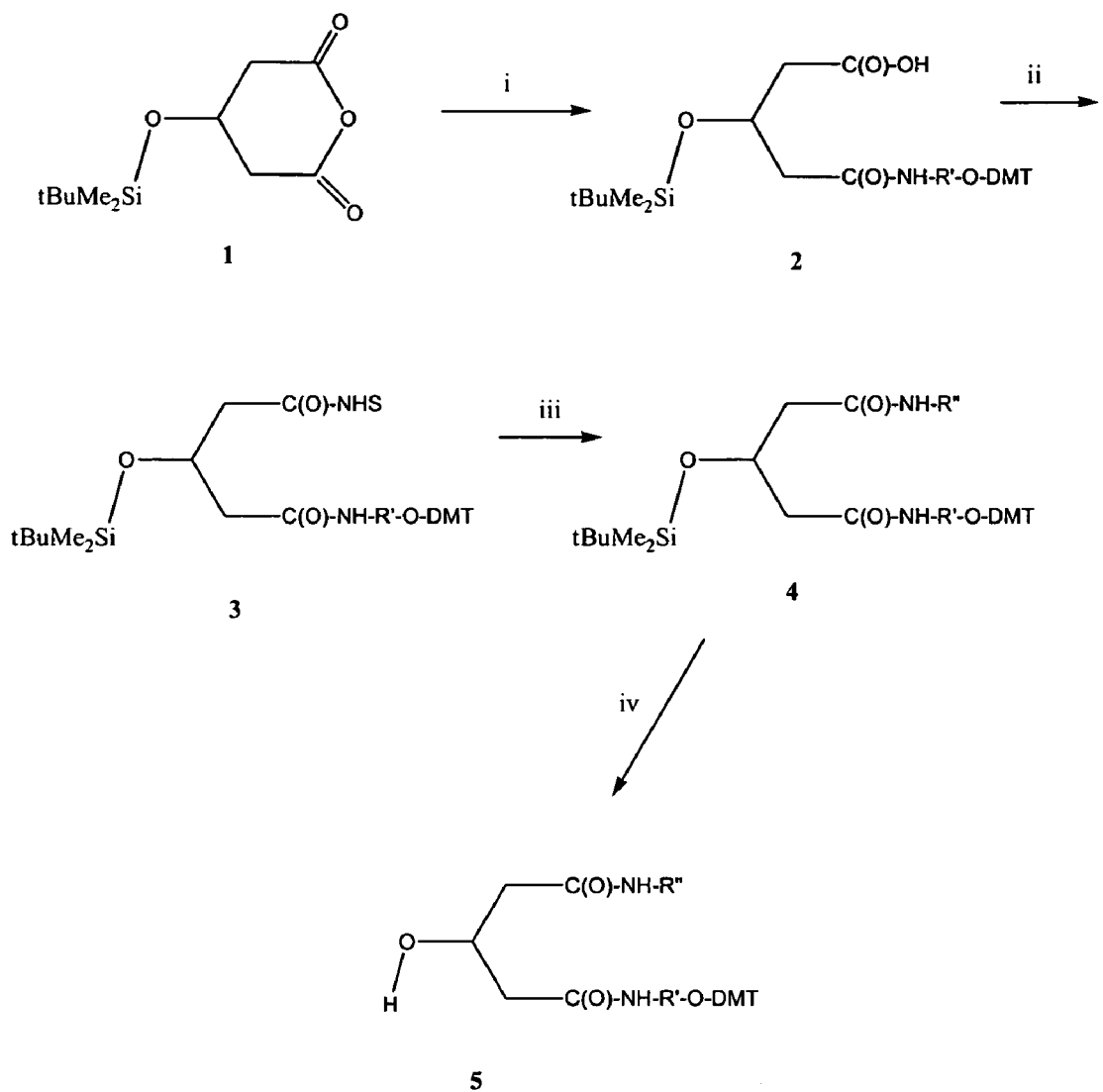
FIG. 1 shows synthesis of compounds of some embodiments of the present invention. Synthesis of compounds 2, 3, 4 and 5 is shown; (i) $H_2N$—R'—O-DMT/base; (ii) NHS/DCC; (iii) $H_2N$—R"/base; (iv) TBAF/THF.

As used herein, the terms "X, Y, $R_1$ and $R_2$" refer to any atom or molecule attached to another molecule (e.g., a reagent of the present invention), unless specifically identified otherwise.

As used herein, the term "nucleic acid labeling reagent" refers to any reagent that is used to introduce a modification into a nucleic acid (e.g., an oligonucleotide). In some embodiments nucleic acid labeling reagents include, but are not limited to, modified synthesis solid supports, modified phosphoramidites, and modified linkers. The nucleic acid labeling reagents of the present invention may be used to introduce any desired modification (e.g., including, but not limited to, "labels" and biological molecules) into a nucleic acid.

The term "label" as used herein refers to any atom or molecule that can be used to provide a detectable (preferably quantifiable) effect, and that can be attached to a nucleic acid or protein. Labels include but are not limited to dyes; radiolabels such as $^{32}P$; binding moieties such as biotin; haptens such as digoxgenin; luminogenic, phosphorescent or fluorogenic moieties; and fluorescent dyes alone or in combination with moieties that can suppress or shift emission spectra by fluorescence resonance energy transfer (FRET). Labels may provide signals detectable by fluorescence, radioactivity, colorimetry, gravimetry, X-ray diffraction or absorption, magnetism, enzymatic activity, and the like. A label may be a charged moiety (positive or negative charge) or alternatively, may be charge neutral. Labels can include or consist of nucleic acid or protein sequence, so long as the sequence comprising the label is detectable.

As used herein, the terms "solid support" or "support" refer to any material that provides a solid or semi-solid structure with which another material can be attached. Such materials include smooth supports (e.g., metal, glass, plastic, silicon, and ceramic surfaces) as well as textured and porous materials. Such materials also include, but are not limited to, gels, rubbers, polymers, and other non-rigid materials. Solid supports need not be flat. Supports include any type of shape including spherical shapes (e.g., beads). Materials attached to solid support may be attached to any portion of the solid support (e.g., may be attached to an interior portion of a porous solid support material). In some embodiments, solid supports are used for the synthesis of nucleic acid. In such embodiments, a preferred material for a solid support is controlled pore glass (CPG). A molecule (e.g., the nucleic acid labeling reagents of the present invention) is "attached" to a solid support when it is associated with the solid support through a non-random chemical or physical interaction. In some preferred embodiments, the attachment is through a covalent bond. However, attachments need not be covalent or permanent. In some embodiments, materials are attached to a solid support through a "spacer molecule" or "linker group." Such spacer molecules are molecules that have a first portion that attaches to the molecule and a second portion that attaches to the solid support. Thus, when attached to the solid support, the spacer molecule separates the solid support and the molecule, but is attached to both.

As used herein, the term "nucleic acid molecule" refers to any nucleic acid containing molecule, including but not limited to, DNA (single and double-stranded), RNA (single and double-stranded), and protein nucleic acid (PNA). The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc).

As used herein, the term "sample template" refers to nucleic acid originating from a sample that is analyzed for the presence of "target." In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (e.g., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer should be sufficiently long to prime the synthesis of extension products in the presence of the inducing agent. The exact lengths of the primers will depend on many factors, including temperature, source of primer and the use of the method.

As used herein, the term "probe" refers to an oligonucleotide, whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that probes used in the present invention can be labeled with a "reporter molecule," so that they are detectable in a detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target" refers to the region of nucleic acid that is sought to be sorted out from other nucleic acid sequences. A "probe" is sometimes, but not always, designed to be complementary to the "target." In some embodiments, the target nucleic acid is a region containing a mutation or polymorphism of interest.

As used herein, the term "polymerase chain reaction" ("PCR") refers to the method of K. B. Mullis U.S. Pat. Nos. 4,683,195 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process are, themselves, efficient templates for subsequent PCR amplifications. As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

DETAILED DESCRIPTION OF THE INVENTION

The present invention provides preparative methods for the synthesis of nucleic acid probes modified internally or at their 3' or 5'-ends with diverse modifications. In some embodiments, the synthetic strategy of the present invention provides a new family of phosphoramidites and solid supports that are compatible with the automated synthesis of modified oligonucleotides. In some preferred embodiments, these novel reagents are prepared from a common intermediate obtained from commercially available 3-(tert-butyldimethylsiloxy)

glutaric anyhdride. In some embodiments, these novel reagents are used to synthesize phosphoramidites. In further embodiments, the novel reagents of the present invention are used to synthesize variable length linkers. In yet other embodiments, the novel reagents of the present invention are used to attach nucleic acids to a solid support or other materials or molecules (e.g. biological molecules).

I. Reagents

In some embodiments, the present invention provides reagents for use in the production of modified nucleic acids. Experiments conducted during the course of development of the present invention resulted in the synthesis of novel reagents useful in the labeling of nucleic acids in a wide variety of methods.

In some embodiments, commercially available 3-(tert-butyldimethylsiloxy) glutaric anyhdride 1 is used as a starting material for the preparation of the novel labeling reagents of the present invention. Exemplary synthesis methods utilizing the reagent of the present invention are provided in the experimental section below. These methods, as well as the exemplary labeled nucleic acids, are merely exemplary embodiments of the present invention. One skilled in the relevant arts understands that the compositions and methods of the present invention find use in the synthesis of a variety of labeled nucleic acids utilizing a variety of synthetic methods.

II. Modified Nucleic Acids

The reagents of the present invention find use in the synthesis of modified nucleic acids, for the preparation of new types of variable length linkers in nucleic acids, for the conjugation of biomolecules to nucleic acids and for the attachment of nucleic acids to solid supports. In some embodiments, the labeled nucleic acids or linkers comprise functionalities that serve as starting materials in conjugation reactions with other organic moieties. In some preferred embodiments, the reagents of the present invention introduce a functionality (e.g., hydrazido groups, aminooxy groups, thiol groups, carboxy groups, phosphorothioates, heteroatoms, or aldehydes). In other preferred embodiments, the labeled nucleic acids or linkers of the present invention comprise modifications including, but not limited to, dyes, peptides, ligands, organic moieties, and biological molecules, and varying linker lengths. In some particularly preferred embodiments, the labeled nucleic acids or linkers of the present invention comprise biotin.

A. Modified Solid Supports

In recent years, chemical literature has reported numerous methods for synthesizing different phosphoramidite reagents used to introduce single or multiple functional groups at the 3' or 5' terminus of a synthesized DNA oligonucleotide (Guzayev et al., (1995) Tetrahedron 51, 9375-9384; Matray et al., (1997) Bioconjugate Chem. 8:99-102; Lyttle et al., (1997) Bioconjugate Chem. 8:193-198). In contrast, far fewer methods are reported for utilizing a specifically modified solid support to synthesize 3'-modified oligonucleotides (Habus et al., (1998) Bioconjugate Chem. 9: 283-291; Stetsenko et al., (2001) Bioconjugate Chem. 12:576-586; Hausch and Jäschke (2001) Tetrahedron 57:1261-1268), most likely due to the synthetic inconveniences associated with the preparation of such reagents. In some embodiment, the methods of the present invention utilize the approach of synthesizing a NHS ester key intermediate that can be used to prepare solid supports modified with a functional group. In some embodiments, such functional groups comprise amino groups, thiol groups, carboxy groups, phosphorothioates, heteroatoms, or aldehydes.

In other preferred embodiments, the methods of the present invention are used to synthesize a NHS ester key intermediate which can be used to prepare solid supports modified with an organic moiety. In some preferred embodiments, the organic moiety includes, but is not limited to, dyes, peptides, ligands, organic moieties, and biological molecules, and variable length linkers.

In some embodiments, the present invention provides solid supports (e.g., CPG) modified with a reagent of the present invention. Such modified solid supports find use in the modification of synthesized nucleic acids at the 3' or 5' end. For example, in some embodiments, the TBDMS group is removed to yield a compound possessing a deprotected secondary hydroxyl group. In some embodiments, this deprotected secondary hydroxyl group is reacted to generate a modified solid support. In some embodiments, the modified solid support is a CPG. Exemplary synthesis methods are described in the experimental section (See e.g., FIGS. 2 and 4). FIGS. 5, 7, 9 and 12 demonstrate exemplary modified oligonucleotides made according to the methods of the present invention.

In still other embodiments, the present invention provides modified solid supports comprising variable length linkers. In some embodiments, linkers are used to attach labels to nucleic acids (e.g., fluorescent or affinity labels). In other embodiments, linkers are used to attach any number of different biological molecules to oligonucleotides (e.g., proteins, lipids, carbohydrates, etc.) or to attach oligonucleotides to solid supports.

B. Modified Phosphoramidites and Oligonucleotides

In some embodiments, the reagents of the present invention are utilized in the synthesis of phosphoramidites. FIGS. 2, 3, 11, and 12 demonstrate exemplary synthesis methods for preparing a phosphoramidite that includes an R group of interest. In some embodiments, the phosphoramidites are then used in automated synthesis methods to generate modified oligonucleotides. FIGS. 5, 7, 9 and 12 demonstrate exemplary modified oligonucleotides made according to the methods of the present invention. In some embodiments, the labeled oligonucleotides serve as starting materials in conjugation reactions with other organic moieties containing compatible functional groups. In some preferred embodiments, these functional groups include, but are not limited to, amino groups, hydrazido groups, aminooxy groups, thiol groups, carboxy groups, phosphorothioates, heteroatoms, and aldehydes.

In some embodiments, the modified phosphoramidites of the present invention comprise variable length linkers. In some embodiments, variable length linkers are used in the preparation of specific nucleic acids or conjugates.

III. Applications

The modified nucleic acids of the present invention find use in any number of applications utilizing the labeling and detection of nucleic acids. The advent of large scale genomic projects and the increasing medical use of molecular diagnostics has prompted the development of large volume throughput methods for screening recombinant DNA libraries representing entire genomes, the performance of large scale DNA sequencing projects, and executing replicative immunological assays, nucleic acid hybridization assays, or polymerase chain reaction assays. High throughput methods often rely on biomolecular arrays.

Many disease states are characterized by differences in the expression levels of various genes either through changes in the copy number of the gene's DNA or through changes in levels of transcription (e.g., through control of initiation, provision of RNA precursors, RNA processing, etc.) of particular genes. For example, losses and gains of genetic material play an important role in malignant transformation and progression. These gains and losses are thought to be "driven" by at least two kinds of genes. Oncogenes are positive regulators of tumorgenesis, while tumor suppressor genes are negative regulators of tumorgenesis (Marshall, Cell, 64: 313-326 (1991); Weinberg, Science, 254: 1138-1146 (1991)). Thus, changes in the expression (transcription) levels of particular genes (e.g. oncogenes or tumor suppressors), serve as signposts for the presence and progression of various cancers. Similarly, control of the cell cycle and cell development, as well as diseases, are characterized by the variations in the transcription levels of particular genes. Thus, for example, a viral infection is often characterized by the elevated expression of genes of the particular virus. Detection of elevated expression levels of characteristic viral genes provides an effective diagnostic of the disease state. In particular, viruses such as herpes simplex, enter quiescent states for periods of time only to erupt in brief periods of rapid replication. Detection of expression levels of characteristic viral genes allows detection of such active proliferative (and presumably infective) states. Exemplary, non limiting methods are described below.

A. Immobilization on a Solid Support

In some embodiments, the reagents of the present invention (e.g., the linkers described above) are used in the immobilization of nucleic acids on solid supports. Immobilized nucleic acids are used in many applications including, but not limited to, gene expression analysis, drug screening, nucleic acid sequencing, and mutation analysis. In some embodiments, arrays of nucleic acids are used in such applications.

B. Diagnostic Applications

In some embodiments, the labeled nucleic acids of the present invention find use in diagnostic applications (e.g., the detection of target nucleic acids). In some embodiments of the present invention, nucleic acid sequences labeled using the compositions and methods of the present invention are used in the detection of nucleic acid sequences. For example, in some embodiments, labeled nucleic acid sequences are hybridized to target nucleic acid sequences in a hybridization assay. In a hybridization assay, the presence or absence of a target nucleic acid sequence is determined based on the ability of the nucleic acid from the sample to hybridize to a complementary nucleic acid molecule (e.g., a oligonucleotide probe labeled using the compositions and methods of the present invention). A variety of hybridization assays using a variety of technologies for hybridization and detection are suitable for use in the detection of target nucleic acids. A description of a selection of assays is provided below.

a. Direct Detection of Hybridization

In some embodiments, hybridization of a nucleic acid sequence labeled using the compositions and methods of the present invention to the target sequence of interest is detected directly by visualizing a bound probe comprising a fluorescent or other label (e.g., a Northern or Southern assay; See e.g., Ausabel et al. (eds.), Current Protocols in Molecular Biology, John Wiley & Sons, NY [1991]). In these assays, genomic DNA (Southern) or RNA (Northern) is isolated from a subject. The DNA or RNA is then cleaved with a series of restriction enzymes that cleave infrequently in the genome and not near any of the markers being assayed. The DNA or RNA is then separated (e.g., on an agarose gel) and transferred to a membrane. A nucleic acid sequence labeled using the compositions and methods of the present invention specific for the target nucleic acid sequence being detected is allowed to contact the membrane under conditions of low, medium, or high stringency. Unbound labeled nucleic acid is removed and the presence of binding is detected by visualizing the labeled nucleic acid.

b. Detection of Hybridization Using "DNA Chip" Assays

In some embodiments of the present invention, target sequences are detected using a DNA chip hybridization assay. In this assay, a series of nucleic acid probes are affixed to a solid support. Each of the probes is designed to be unique to a given target sequence. The DNA sample of interest is contacted with the DNA "chip" and hybridization is detected.

In some embodiments, the DNA chip assay is a GeneChip (Affymetrix, Santa Clara, Calif.; See e.g., U.S. Pat. Nos. 6,045,996; 5,925,525; and 5,858,659; each of which is herein incorporated by reference) assay. The GeneChip technology uses miniaturized, high-density arrays of oligonucleotide probes affixed to a "chip." Probe arrays are manufactured by Affymetrix's light-directed chemical synthesis process, which combines solid-phase chemical synthesis with photolithographic fabrication techniques employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays are synthesized simultaneously on a large glass wafer. The wafers are then diced, and individual probe arrays are packaged in injection-molded plastic cartridges, which protect them from the environment and serve as chambers for hybridization.

In some embodiments, the nucleic acid to be analyzed is isolated, amplified by PCR, and labeled using the compositions and methods of the present invention. The labeled DNA is then incubated with the array using a fluidics station. The array is then inserted into a scanner, where patterns of hybridization are detected. The hybridization data are collected as light emitted from the fluorescent reporter groups already incorporated into the target, which is bound to the probe array. Probes that perfectly match the target generally produce stronger signals than those that have mismatches. Since the sequence and position of each probe on the array are known, by complementarity, the identity of the target nucleic acid applied to the probe array can be determined.

In other embodiments, a DNA microchip containing electronically captured probes (nucleic acid sequences labeled using the compositions and methods of the present invention) (Nanogen, San Diego, Calif.) is utilized (See e.g., U.S. Pat. Nos. 6,017,696; 6,068,818; and 6,051,380; each of which are herein incorporated by reference). Through the use of microelectronics, Nanogen's technology enables the active movement and concentration of charged molecules to and from designated test sites on its semiconductor microchip. DNA capture probes unique to a given SNP or mutation are electronically placed at, or "addressed" to, specific sites on the microchip. Since DNA has a strong negative charge, it can be electronically moved to an area of positive charge.

First, a test site or a row of test sites on the microchip is electronically activated with a positive charge. Next, a solution containing the DNA probes is introduced onto the microchip. The negatively charged probes rapidly move to the positively charged sites, where they concentrate and are chemically bound to a site on the microchip. The microchip is then washed and another solution of distinct DNA probes is added until the array of specifically bound DNA probes is complete.

A test sample is then analyzed for the presence of target DNA molecules by determining which of the DNA capture probes hybridize with complementary DNA in the test sample (e.g., a PCR amplified gene of interest). An electronic charge is also used to move and concentrate target molecules to one or more test sites on the microchip. The electronic concentration of sample DNA at each test site promotes rapid hybridization of sample DNA with complementary capture probes (hybridization may occur in minutes). To remove any unbound or nonspecifically bound DNA from each site, the polarity or charge of the site is reversed to negative, thereby forcing any unbound or nonspecifically bound DNA back into solution away from the capture probes. In some embodiments, a laser-based fluorescence scanner is then used to detect binding.

In still further embodiments, an array technology based upon the segregation of fluids on a flat surface (chip) by differences in surface tension (ProtoGene, Palo Alto, Calif.) is utilized (See e.g., U.S. Pat. Nos. 6,001,311; 5,985,551; and 5,474,796; each of which is herein incorporated by reference). Protogene's technology is based on the fact that fluids can be segregated on a flat surface by differences in surface tension that have been imparted by chemical coatings. Once so segregated, oligonucleotide probes are synthesized directly on the chip by ink-jet printing of reagents. The array with its reaction sites defined by surface tension is mounted on a X/Y translation stage under a set of four piezoelectric nozzles, one for each of the four standard DNA bases. The translation stage moves along each of the rows of the array and the appropriate reagent is delivered to each of the reaction site. For example, the A amidite is delivered only to the sites where amidite A is to be coupled during that synthesis step and so on. Common reagents and washes are delivered by flooding the entire surface and removing by spinning.

DNA probes unique for the target sequence of interest are affixed to the chip using Protogene's technology. The chip is then contacted with the PCR-amplified genes of interest. Following hybridization, unbound DNA is removed and hybridization is detected using any suitable method (e.g., by fluorescence de-quenching of an incorporated fluorescent group).

In yet other embodiments, a "bead array" is used for the detection of polymorphisms (Illumina, San Diego, Calif.; See e.g., PCT Publications WO 99/67641 and WO 00/39587, each of which is herein incorporated by reference). Illumina uses a BEAD ARRAY technology that combines fiber optic bundles and beads that self-assemble into an array. Each fiber optic bundle contains thousands to millions of individual fibers depending on the diameter of the bundle. The beads are coated with an oligonucleotide specific for the detection of a given target sequence. Batches of beads are combined to form a pool specific to the array. To perform an assay, the BEAD ARRAY is contacted with a prepared subject sample (e.g., DNA). Hybridization is detected using any suitable method.

c. Enzymatic Detection of Hybridization

In some embodiments, hybridization is detected by enzymatic cleavage of specific structures (e.g., the INVADER assay, Third Wave Technologies; See e.g., U.S. Pat. Nos. 5,846,717, 6,090,543; 6,001,567; 5,985,557; and 5,994,069; each of which is herein incorporated by reference). The INVADER assay detects specific DNA and RNA sequences by using structure-specific enzymes to cleave a complex formed by the hybridization of overlapping oligonucleotide probes. Elevated temperature and an excess of one of the probes enable multiple probes to be cleaved for each target sequence present without temperature cycling. These cleaved probes then direct cleavage of a second labeled probe. In some embodiments, the secondary probe oligonucleotide is 5'-end labeled using the compositions and methods of the present invention that is quenched by an internal dye. Upon cleavage, the de-quenched labeled product may be detected using a standard fluorescence plate reader.

The INVADER assay detects specific target sequences in unamplified genomic DNA. The isolated DNA sample is contacted with the first probe specific for the target sequence of interest and allowed to hybridize. Then a secondary probe, specific to the first probe, and containing the fluorescent or other label, is hybridized and the enzyme is added. Binding is detected by using a fluorescent plate reader and comparing the signal of the test sample to known positive and negative controls.

In other embodiments, hybridization of a bound probe is detected using a TaqMan assay (PE Biosystems, Foster City, Calif.; See e.g., U.S. Pat. Nos. 5,962,233 and 5,538,848, each of which is herein incorporated by reference). The assay is performed during a PCR reaction. The TaqMan assay exploits the 5'-3' exonuclease activity of the AMPLITAQ GOLD DNA polymerase. A probe, specific for a given target sequence, is included in the PCR reaction. The probe consists of an oligonucleotide with a 5'-reporter dye (e.g., labeled using the compositions and methods of the present invention) and a 3'-quencher dye. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In still further embodiments, target sequences are detected using the SNP-IT primer extension assay (Orchid Biosciences, Princeton, N.J.; See e.g., U.S. Pat. Nos. 5,952,174 and 5,919,626, each of which is herein incorporated by reference). In this assay, SNPs are identified by using a specially synthesized DNA primer and a DNA polymerase to selectively extend the DNA chain by one base at the suspected SNP location. DNA in the region of interest is amplified and denatured. Polymerase reactions are then performed using miniaturized systems called microfluidics. Detection is accomplished by adding a label (e.g., using the compositions and methods of the present invention) to the nucleotide suspected of being at the target nucleic acid location. Incorporation of the label into the DNA can be detected by any suitable method (e.g., with a fluorimeter).

d. Other Detection Assays

The compositions and methods of the present invention find use in generating labeled nucleic acids for use in additional detection assays including, but not limited to, enzyme mismatch cleavage methods (e.g., Variagenics, U.S. Pat. Nos. 6,110,684, 5,958,692, 5,851,770, herein incorporated by reference in their entireties); polymerase chain reaction; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210,884 and 6,183,960, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (Barnay Proc. Natl. Acad. Sci USA 88, 189-93 (1991)); and sandwich hybridization methods (e.g., U.S. Pat. No. 5,288,609, herein incorporated by reference in its entirety).

In addition, the technologies available from a variety of commercial sources, including, but not limited to, Aclara BioSciences, Haywood, Calif.; Agilent Technologies, Inc., Palo Alto, Calif.; Aviva Biosciences Corp., San Diego, Calif.; Caliper Technologies Corp., Palo Alto, Calif.; Celera, Rockville, Md.; CuraGen Corp., New Haven, Conn.; Hyseq Inc., Sunnyvale, Calif.; Incyte Genomics, Palo Alto, Calif.; Applera Corp., Foster City, Calif.; Rosetta Inpharmatics, Kirkland, Wash.; and Sequenom, San Diego, Calif. are amenable to use with nucleic acid comprising labels incorporated using the compositions and methods of the present invention.

3. In vivo and In situ Applications

In some embodiments, the present invention provides in vivo and in situ methods that utilizing labeled nucleic acids. Such methods find use in the analysis of nucleic acids in cells and populations of cells in culture.

A. FACS

In some embodiments, labels are attached to nucleic acids (e.g., using the compositions and methods of the present invention) that bind to cell surfaces. A computer collects the fluorescence signature of each cell and displays the pattern of fluorescence for the user to analyze. In other applications, where one might want to separate cells which have a certain staining pattern from all other cells (e.g., due to binding to a labeled pre-selected antigen), the flow cytometry machine can direct those desired cells into a tube provided by the user. This is called fluorescence activated cell sorting (FACS).

B. FISH

In some embodiments, nucleic acids labeled using the compositions and methods of the present invention are used in FISH (Fluorescence In-Situ Hybridization) procedures. A FISH sample is prepared by using multiple probes, each of which binds to a different DNA sequence in the chromosomes in the sample. Each probe is labeled with a different dye (e.g., with different colors of emission spectra) or combination of two or more dyes.

EXPERIMENTAL

Example 1

A. Methods
Abbreviations used:
DCC=1,3-Dicyclohexylcarbodiimide
DMAP=4-(Dimethylamino) pyridine
DMF=N,N-Dimethylformamide
EDAC=1-Ethyl-(3-dimethylaminopropyl) carbodiimide hydrochloride
HBTU=O-Benzotriazol-1-yl)-N,N,N',N'-tetramethyluronium
HOBT=1-Hydroxybenzotriazole hydrate
TBAF=Tetrabutylammonium fluoride
TBDMS=tert-Butyldimethylsilyl
TEA=Triethylamine
THF=Tetrahydrofuran
Instruments and Reagents HPLC analyses were performed with a Hitachi D-7000 Interface, L-7100 gradient pump, and L-7400 UV detector using a Varian Omnisphere 5 C18 column (250×4.6 mm) and 100 mM TEAA, pH 7/acetonitrile gradients. MS analysis of all DNA-containing species was performed using a PerSeptive Biosystems Voyager-DE Biospectrometry Workstation V800520. MS analysis of small molecules was performed using an Applied Biosystems/MDS Sciex API 365 LC/MS/MS triple quadrapole with an electrospray ionization source. Automated oligonucleotide synthesis was performed using a PerSeptive Biosystems Expedite Nucleic Acid Synthesis System. Silica gel was obtained from Sigma-Aldrich (Milwaukee, Wis.). Analytical TLC was carried out on EM Science $F_{254}$ glass-backed fluorescence indicator plates. Lcaa-CPG, used in the synthesis of 10c and 10d, was obtained from Glen Research (Sterling, Va.). DNA synthesis reagents and columns were purchased from Applied Biosystems (Foster City, Calif.). All other reagents were purchased from Sigma-Aldrich and used without further purification. Solvents were dried over activated 3 Å molecular sieves.

Synthesis of Ethanolamine Trifluoroacetamide. In a round-bottom flask, methyl trifluoroacetate (10.5 g, 81.9 mmol) was added to neat ethanolamine (4.0 g, 66 mmol) at room temperature with continuous stirring. Reaction completion was determined by the absence of ninhydrin activity. After 2 h, the reaction was concentrated by rotary evaporation and purified by distillation (11 mm Hg, b.p. 127° C.), yielding a colorless oil, 9.5 g, 93%.

Synthesis of O-Dimethoxytrityl Ethanolamine Trifluoroacetamide. Ethanolamine trifluoroacetamide (4.5 g, 29 mmol) was dissolved in 100 ml pyridine in a round-bottom flask. With stirring, 4, 4'-dimethoxytrityl chloride (9.7 g, 29 mmol) was added to the solution as a solid. After stirring 2 h, the slurry was filtered, and the filtrate was concentrated by rotary evaporation. The residue was purified by silica column chromatography (25% ethyl acetate/75% hexane). The product was obtained as a yellow oil (12 g, 91%). $R_f$=0.56 (25% ethyl acetate/75% hexane).

Synthesis of O-Dimethoxytrityl Ethanolamine. O-Dimethoxytrityl ethanolamine trifluoroacetamide (12 g, 26 mmol) was dissolved in 400 ml methanol. Subsequently, 400 ml of concentrated ammonium hydroxide was added to the flask with continuous stirring. The reaction mixture was stirred for 16 h at room temperature. The mixture was concentrated by rotary evaporation, and the crude product was purified by silica column chromatography (2% methanol/5% TEA/methylene chloride), yielding a yellow oil, 9.2 g, 97%. $R_f$=0.41 (5% methanol/5% TEA/methylene chloride). $^1$H NMR, $CD_3CN$, 400 MHz, δ 7.45 (m, 2H), 7.31 (m, 6H), 7.22 (t, 1H), 6.86 (m, 4H), 3.76 (s, 6H), 3.02 (t, 2H), 2.78 (t, 2H), 2.07 (s, 2H) ppm. ESI-MS: calculated for $C_{23}H_{24}NO_3$ (M+K)$^+$ 402, found 402.

Synthesis of 2, R'=$CH_2CH_2$. A 250 ml round-bottom flask was charged with O-dimethoxytrityl ethanolamine (4.0 g, 11 mmol), N,N-diisopropylethylamine (2.1 g, 16 mmol), and 50 ml of acetonitrile. 3-(tert-Butyldimethylsilyloxy)glutaric anhydride 1 (3.0 g, 12 mmol) was added as a solid with stirring. After 2 h, the reaction was concentrated and the crude material was purified by silica column chromatography (2% methanol/5% TEA/methylene chloride), yielding a white solid, 6.4 g, 96%. $R_f$=0.35 (2% methanol/5% TEA/methylene chloride). $^1$H NMR, $CD_3CN$, 400 MHz, δ 7.43 (m, 2H), 7.30 (m, 6H), 7.22 (m, 1H), 6.85 (m, 5H), 4.96 (s, 1H), 4.42 (m, 1H), 3.76 (s, 6H), 3.35 (m, 2H), 3.04 (m, 2H), 2.40 (m, 4H), 0.82 (s, 9H), 0.05 (s, 3H), 0.01 (s, 3H) ppm. ESI-MS: calculated for $C_{34}H_{45}NO_7Si$ (M+K)$^+$ 646, found 646.

Synthesis of 3, R'=CH$_2$CH$_2$. Material 2 (4.8 g, 7.9 mmol) and 100 ml 1,4-dioxane were combined. N-hydroxysuccinimide (1.16 g, 10.1 mmol) and DCC (2.66 g, 12.9 mmol) were added as solids and the reaction was stirred for 1 h. The slurry was filtered and the filtrate was evaporated to a residue that was purified by silica column chromatography (ethyl acetate). Compound 3, R'=CH$_2$CH$_2$, was obtained as an off-white solid (5.2, 93%). $R_f$=0.62 (ethyl acetate). $^1$H NMR, CD$_3$CN, 400 MHz, δ 7.43 (m, 2H), 7.31 (m, 6H), 7.23 (m, 1H), 6.86 (m, 4H), 6.61 (t, 1H), 4.52 (m, 1H), 3.76 (s, 6H), 3.35 (m, 2H), 3.05 (m, 2H), 2.85 (m, 2H), 2.75 (s, 4H), 2.43 (d, 2H), 0.83 (s, 9H), 0.06 (s, 3H), 0.02 (s, 3H) ppm. ESI-MS: calculated for C$_{38}$H$_{48}$N$_2$O$_9$Si (M+K)$^+$ 743, found 743.

One Pot Synthesis of 3, R'=CH$_2$CH$_2$. O-dimethoxytrityl ethanolamine (2.7 g, 7.4 mmol) was added to a solution of 3-(tert-butyldimethylsilyloxy) glutaric anhydride 1 (2.0 g, 8.2 mmol) in THF (100 mL) with stirring. The O-dimethoxytrityl ethanolamine starting material was consumed after 1 h (TLC 5% methanol/5% TEA/methylene chloride), and N-hydroxysuccinimide (0.94 g, 8.2 mmol) and DCC (2.3 g, 11 mmol) were added to the reaction mixture. After 4 h, the reaction slurry was filtered, and the filtrate was concentrated. The crude residue was purified by silica column chromatography (50% ethyl acetate/50% hexane) and the product was isolated as an off-white solid (3.8 g, 73%). $R_f$=0.62 (ethyl acetate). ESI-MS: calculated for C$_{38}$H$_{48}$N$_2$O$_9$Si (M+K)$^+$ 743, found 743.

Synthesis of 4a. Compound 3, R'=CH$_2$CH$_2$, (0.55 g, 0.78 mmol) was combined with 1.5 ml THF and dried overnight over activated sieves. 2-(aminoethyl)-18-crown-6 (0.25 g, 0.85 mmol) was dissolved in 20 ml THF and combined with the THF solution of 3. The reaction mixture was stirred for 1 h, concentrated by rotary evaporation, and purified by silica column chromatography (5% methanol/5% TEA/methylene chloride), yielding a pale yellow solid 0.68 g, 99%. $R_f$=0.32 (5% methanol/5% TEA/methylene chloride). ESI-MS: calculated for C$_{47}$H$_{70}$N$_2$O$_{12}$Si (M+K)$^+$ 922, found 922.

Synthesis of 11. N-hydroxysuccinimide (0.27 g, 2.3 mmol) and DCC (0.48 g, 2.3 mmol) were added to a solution of 1-pyrenebutyric acid (0.58 g, 2.0 mmol) in 1, 4-dioxane (20 ml). The solution was stirred for 20 h at room temperature. Ethyl acetate (30 ml) was added and the slurry was filtered. The filtrate was concentrated, and the resulting brown oil was used in the next step without further purification, 0.77 g. $R_f$=0.38 (50% ethyl acetate/50% hexane). A solution of the prepared NHS ester of 1-pyrene butyric acid (0.77 g, 2.0 mmol) in 1, 4-dioxane (20 ml) was added to a solution of 4, 7, 10-trioxa-1, 13-tridecanediamine (2.6 g, 12 mmol) in 1,4-dioxane (20 ml). The resulting solution was stirred for 1 h, concentrated by rotary evaporation, and purified by silica column chromatography (10% methanol/5% TEA/methylene chloride). Compound 11 was obtained as an oil (0.89 g, 90%). $R_f$=0.33 (10% methanol/5% TEA/methylene chloride). ESI-MS: calculated for C$_{30}$H$_{38}$N$_2$O$_4$ (M+H)$^+$ 491, found 491.

Synthesis of 4b: A solution of 11 (0.89 g, 1.8 mmol) in acetonitrile (5 ml), THF (5 ml), and diisopropylethylamine (0.26 g, 2.0 mmol) was combined with a solution of 3, R'=CH$_2$CH$_2$, (1.2 g, 1.7 mmol) in THF (30 ml). The reaction mixture was concentrated after 1 h by rotary evaporation. The crude residue was purified by silica chromatography (5% methanol/5% TEA/methylene chloride), resulting in a pale yellow solid with a yield of 1.2 g, 68%. $R_f$=0.52 (5% methanol/5% TEA/methylene chloride). ESI-MS: calculated for C$_{64}$H$_{81}$N$_3$O$_{10}$Si(M+Na)$^+$ 1103, found 1103.

Synthesis of 4c. A solution of 3, R'=CH$_2$CH$_2$, (3.1 g, 4.4 mmol) in 1, 4-dioxane (5 ml) and acetonitrile (30 ml) was added to a solution of 4, 7, 10-trioxa-1, 13-tridecanediamine (3.8 g, 17 mmol) in acetonitrile (20 ml). The resulting slurry was stirred for 30 minutes, concentrated by rotary evaporation and purified by silica column chromatography (10% methanol/5% TEA/methylene chloride) with a yield of 1.4 g, 40%. The product was confirmed by a positive ninhydrin test. $R_f$=0.34 (10% methanol/5% TEA/methylene chloride). ESI-MS: calculated for C$_{44}$H$_{67}$N$_3$O$_9$Si (M+H)$^+$ 811, found 811.

Synthesis of 12c. Biotin (0.86 g, 3.5 mmol), DMF (5 ml) diisopropylethylamine (1.4 g, 11 mmol), and HOBT (0.96 g, 7.2 mmol) were added to a round-bottom flask with stirring. A solution of 4c (1.4 g, 1.8 mmol) in methylene chloride (5 ml) was added to the flask and HBTU (1.2 g, 3.7 mmol) was added to the resulting mixture. After 2 h, the reaction mixture was concentrated and purified by silica column chromatography (10% methanol/5% TEA/methylene chloride). The product was obtained as an oil (1.5 g, 80%). $R_f$=0.44 (10% methanol/5% TEA/methylene chloride). ESI-MS: calculated for C$_{54}$H$_{81}$N$_5$O$_{11}$SSi (M+Na)$^+$1059, found 1059.

Synthesis of 4d. Compound 3, R'=CH$_2$CH$_2$, (0.62 g, 0.88 mmol) was dissolved in 1, 4-dioxane (10 ml) and added to a solution of polytetrahydrofuran-bis-(3-aminopropyl) terminated, average M$_n$ ca. 1100 (3.9 g, 3.5 mmol) in 1, 4-dioxane (20 ml). After stirring for 2 h, the solvent was evaporated and the residue was purified by silica column chromatography (7.5% methanol/5% TEA/methylene chloride), yielding an oil, 0.85 g, 57%. $R_f$=0.44 (7.5% methanol/5% TEA/methylene chloride). MALDI-TOF MS: The mass dispersion of the starting bis-amine was centered at 580. The mass dispersion of the products (separated by 72 amu) was centered at 1190.

Synthesis of 12d. To a solution of 4d (0.85 g, 0.71 mmol) in acetonitrile (10 ml) and THF (5 ml) was added diisopropylethylamine (0.26 g, 2.0 mmol) and S-ethyl-trifluorothioacetate (0.32 g, 0.20 mmol) with stirring. The absence of ninhydrin activity after 3.5 h confirmed the complete protection of the amine group. The reaction mixture was concentrated and purified by silica column chromatography (7.5% methanol/5% TEA/methylene chloride). Desired product was isolated as an oil, 0.78 g, 85%. $R_f$=0.46 (7.5% methanol/5% TEA/methylene chloride). ESI-MS: The mass dispersion of the products (separated by 72 amu) was centered at 1290.

Synthesis of 5a. Compound 4a (0.68 g, 0.77 mmol) was dissolved in 10 ml TBAF (1.0M in THF) and incubated for 20 minutes at room temperature. The solvent was evaporated and the residue was purified by silica column chromatography (5% methanol/5% TEA/methylene chloride), yielding a pale yellow oil, 0.38 g, 64%. $R_f$=0.29 (5% methanol/5% TEA/methylene chloride). ESI-MS: calculated for C$_{41}$H$_{56}$N$_2$O$_{12}$ (M+K)$^+$ 808, found 808.

Synthesis of 5b. Compound 4b (1.2 g, 1.1 mmol) was dissolved in THF (5 ml) and TBAF (5 ml of 1.0M in THF) was added to the resulting solution. The reaction mixture was incubated for 30 minutes, concentrated, and the residue was purified by silica column chromatography (2% methanol/5% TEA/methylene chloride). Material 5b was obtained as an off-white solid (0.66 g, 60%). $R_f$=0.58 (5% methanol/5% TEA/methylene chloride). ESI-MS: calculated for C$_{58}$H$_{67}$N$_3$O$_{10}$ (M+H)$^+$ 967, found 967.

Synthesis of 5c. Compound 12c (1.5 g, 1.4 mmol) was dissolved in THF (5 ml), and TBAF (5 ml of 1.0M in THF) was added to the resulting mixture. The reaction mixture was incubated for 1 h, concentrated, and the residue was purified by silica column chromatography (10% methanol/5% TEA/methylene chloride), yielding an oil, 1.3 g, 94%. $R_f$=0.32 (10% methanol/5% TEA/methylene chloride). ESI-MS: calculated for C$_{48}$H$_{67}$N$_5$O$_{11}$S (M+K)$^+$ 961, found 961.

Synthesis of 5d. Compound 12d (0.50 g, 0.43 mmol) was dissolved in 10 ml TBAF (1.0M in THF) and incubated for 15 minutes at room temperature. The solvent was evaporated and the residue was purified by silica column chromatography (5% methanol/5% TEA/methylene chloride). Material 5d was obtained as a pale brown solid (0.44 g, 98%). $R_f$=0.49 (5% TEA/1, 4-dioxane). MALDI-TOF MS: The mass dispersion of the products (separated by 72 amu) was centered at 1170.

Synthesis of 18. N-hydroxysuccinimide (0.50 g, 4.3 mmol) and DCC (1.5 g, 7.3 mmol) were added to a vigorously stirred suspension of p-(p-dimethylaminophenylazo) benzoic acid, sodium salt (1.0 g, 3.4 mmol) in anhydrous 1, 4-dioxane (30 ml). The resulting reaction mixture was stirred overnight at room temperature and subsequently diluted with 100 ml of dry ethyl acetate. The slurry was filtered and the filtrate was concentrated yielding the dabcyl-NHS ester (1.1 g, 87%) as a dark red powder. TLC analysis confirmed the purity of the material. $R_f$=0.54 (ethyl acetate). The isolated NHS active ester was dissolved in THF (50 ml) and immediately added to a vigorously stirred solution of 4, 7, 10-trioxa-1, 13-tridecanediamine (10 g, 0.045 mol) in THF (250 ml). The resulting reaction mixture was stirred at room temperature for 2 h and concentrated by rotary evaporation. Compound 18 was isolated by silica column chromatography (20% methanol/5% TEA/methylene chloride) as an orange solid (0.33 g, 26%). $R_f$=0.30 (20% methanol/5% TEA/methylene chloride). ESI-MS: calculated for $C_{25}H_{37}N_5O_4$ (M+H)$^+$ 472, found 472.

One Pot Synthesis of 21. 3-(tert-Butyldimethylsilyloxy) glutaric anhydride (0.20 g, 8.2 mmol) was added to a rapidly stirred solution of compound 18 (0.33 g, 7.1 mmol) and N, N-diisopropylethylamine (0.10 g, 7.8 mmol) in 10 ml of 1, 4-dioxane. After 15 minutes, TLC analysis indicated the disappearance of the starting material and the formation of a new product, $R_f$=0.48 (10% methanol/5% TEA/methylene chloride). In the subsequent step, N-hydroxysuccinimide (0.12 g, 1.0 mmol) and DCC (0.42 g, 2.0 mmol) were added to the reaction mixture. The DCC was added in two aliquots, 0.22 g initially and 0.20 g after 1 h. The resulting reaction mixture was stirred at room temperature for an additional 15 h. TLC analysis of the reaction mixture indicated the formation of a new, less polar material, $R_f$=0.58 (1, 4-dioxane). In the final step, 2-(2-aminoethoxyethyl) ethanol (0.73 g, 7.0 mmol) was dissolved in 4 ml of dry THF and added to the rapidly stirred reaction mixture described above. Stirring was continued for 1 h at room temperature. TLC analysis indicated the formation of a new product, $R_f$=0.38 (1, 4-dioxane). The reaction product was isolated by silica column chromatography (1, 4-dioxane), yielding compound 21 as an orange solid (0.48 g, 85%). ESI-MS: calculated for $C_{40}H_{66}N_6O_9Si$ (M+H)$^+$ 804, found 804.

Synthesis of 22. Compound 21 (0.44 g, 0.55 mmol) was dissolved in 100 ml pyridine in a round-bottom flask. With stirring, 4, 4'-dimethoxytrityl chloride (0.30 g, 0.90 mmol) was added to the solution as a solid. After stirring 2 h, the solution was concentrated by rotary evaporation. The residue was purified by silica column chromatography (ethyl acetate followed by 2% methanol/5% TEA/methylene chloride). The product was obtained as an orange solid (0.40 g, 66%). $R_f$=0.20 (5% methanol/5% TEA/methylene chloride). ESI-MS: calculated for $C_{61}H_{84}N_6O_{11}Si$ (M+K)$^+$ 1144, found 1144.

Synthesis of 5e. Compound 22 (0.40 g, 0.36 mmol) was dissolved in THF (5 ml) and tetrabutylammonium fluoride (7 ml of 1.0M in THF) was added to the resulting solution. The reaction mixture was incubated for 30 minutes, concentrated, and the residue was purified by silica column chromatography (2% methanol/5% TEA/methylene chloride followed by 5% methanol/5% TEA/methylene chloride and finally 10% methanol/5% TEA/methylene chloride to elute the product), yielding an orange solid, 0.33 g, 92%. $R_f$=0.67 (5% TEA/1, 4-dioxane). ESI-MS: calculated for $C_{55}H_{70}N_6O_{11}$ (M+K)$^+$ 1030, found 1030.

Synthesis of 8a. Compound 5a (0.38 g, 0.50 mmol) was dissoved in methylene chloride (8 ml) and to the resulting solution added 2-cyanoethyl-N,N,N',N'-tetraisopropyl phosphorodiamidite (0.18 g, 0.59 mmol) and tetrazole (0.83 ml of 0.45M in acetonitrile) with vigorous swirling. The reaction mixture was vortexed at room temperature and after 1 h, additional 2-cyanoethyl-N,N,N',N'-tetraisopropyl phosphorodiamidite (0.18 g, 0.59 mmol) was added. After 1.5 h, methylene chloride (30 ml) was added to the reaction to increase the volume, and the crude solution was washed with 5% sodium bicarbonate/0.5% TEA (50 ml). The organic layer was dried over magnesium sulfate for 10 minutes, filtered, concentrated, and co-evaporated twice with acetonitrile (10 ml). The residue was dissolved in acetonitrile (6 ml) and dried over several granules of calcium hydride. The product solution was aliquoted (3 aliquots of 2 ml, 155 µmol) into amber Expedite bottles, concentrated by aspiration vacuum, then dried overnight under vacuum in a dessicator over phosphorus pentoxide (0.45 g, 94%). $R_f$=0.63 (5% TEA/1, 4-dioxane).

Synthesis of 8b. Material 5b (0.66 g, 0.68 mmol) was dissolved in methylene chloride (5 ml). 2-Cyanoethyl-N,N,N',N'-tetraisopropyl phosphorodiamidite (0.25 g, 0.82 mmol) was added, followed by the addition of tetrazole (1.2 ml of 0.45M in acetonitrile) with vigorous swirling. The reaction was vortexed at room temperature for 3 h. Methylene chloride (50 ml) was added to the reaction to increase the volume, and the crude solution was washed with 5% sodium bicarbonate/ 0.5% TEA (75 ml). The organic layer was dried over magnesium sulfate, filtered, concentrated, and co-evaporated twice with acetonitrile (10 ml). The residue was dissolved in acetonitrile (6 ml) and dried over several granules of calcium hydride. The product solution was aliquoted (3 aliquots of 2 ml, 200 µmol) into amber Expedite bottles, concentrated by aspiration vacuum, then dried overnight under vacuum in a dessicator over phosphorus pentoxide (0.76 g, 96%). $R_f$=0.52 (5% TEA/1, 4-dioxane).

Synthesis of 8e. compound 5e (0.33 g, 0.33 mmol) was dissolved in methylene chloride (10 ml) and to the resulting solution added 2-cyanoethyl-N,N,N',N'-tetraisopropyl phosphorodiamidite (0.15 g, 0.50 mmol) and tetrazole (0.58 ml of 0.45M in acetonitrile) with vigorous swirling. The reaction mixture was vortexed at room temperature, and after 1 h additional 2-cyanoethyl-N,N,N',N'-tetraisopropyl phosphorodiamidite (0.15 g, 0.50 mmol) was added. After 2 h, methylene chloride (50 ml) was added to the reaction to increase the volume, and the crude solution was washed with 5% sodium bicarbonate/0.5% TEA (75 ml). The organic layer was dried over magnesium sulfate for 10 minutes, filtered, concentrated, and co-evaporated twice with acetonitrile (10 ml). The residue was dissolved in acetonitrile (3 ml) and dried over several granules of calcium hydride. The product solution was transferred to an amber Expedite bottles and concentrated by aspiration vacuum then dried for 1 h under vacuum in a dessicator over phosphorus pentoxide (0.37 g, 92%). $R_f$=0.83 (5% TEA/1, 4-dioxane).

Synthesis of 9c. Compound 5c (0.24 g, 0.26 mmol) was combined with TEA (0.03 g, 0.3 mmol), and DMAP (16 mg, 0.13 mmol) in acetonitrile (20 ml). Succinic anhydride (0.04 g, 0.4 mmol) was added and the resulting mixture was stirred for 17 h under a drying tube. The solvent was evaporated and the crude residue was purified by silica column chromatography (10% methanol/5% TEA/methylene chloride). Compound 9c was obtained as a white solid (0.28 g, 95%). $R_f$=0.1 (10% methanol/5% TEA/methylene chloride). ESI-MS: calculated for $C_{52}H_{71}N_5O_{14}S$ (M+H)$^+$ 1123, found 1123.

Synthesis of 9d. Compound 5d (0.44 g, 0.42 mmol) was combined with TEA (0.05 g, 0.5 mmol), and DMAP (26 mg, 0.21 mmol) in acetonitrile (30 ml). Succinic anhydride (0.06 g, 0.6 mmol) was added and the resulting mixture was stirred for 3.5 h under a drying tube. The solvent was evaporated and the crude residue was purified by silica column chromatography (2% methanol/5% TEA/methylene chloride). Compound 9d was obtained as an off-white solid (0.5 g, 96%). $R_f$=0.32 (5% methanol/5% TEA/methylene chloride). MALDI-TOF MS: The mass dispersion of the product was centered at 1270.

Synthesis of 10c and 10d. 1 g lcaa-CPG (Glen Research, #20-0001, 1000A, 69 µmol/g) was added to a 50 ml round-bottom flask. Compound 9c (0.14 g, 0.13 mmol) or compound 9d (0.2 g, 0.16 mmol), respectively, was dissolved in 10 ml pyridine and added to the CPG. DMAP (4 mg, 0.03 mmol), TEA (0.02 g, 0.02 mmol), and EDAC (0.12 g, 0.64 mmol) were added, and the reaction mixtures were vortexed at room temperature for 16 h. For the preparation of 10c, additional aliquots of EDAC (total of 0.1 g, 0.5 mmol) and 9c (total of 0.14 g, 0.13 mmol) were added to the reaction slurry to achieve a final loading of at least 10 µmol/g CPG. For the preparation of 10d, additional aliquots of EDAC (total of 0.40 g, 2.1 mmol) and 9d (total of 0.33 g, 0.26 mmol) were required. The support was filtered, washed with pyridine, methanol, and methylene chloride, and dried with argon flow. The material was capped with an equal mixture of 6% DMAP in acetonitrile and 2/3/5 (acetic anhydride/2,4,6-collidine/acetonitrile) (100 ml total volume) for 2 h and dried overnight under vacuum. The loading was calculated by combining a known mass of CPG and 3% dichloroacetic acid/methylene chloride and measuring $A_{504}$ of the solution to determine the released trityl. The loading of the final products was calculated to be 18 µmol/g CPG and 10 µmol/g CPG for 10c and 10d, respectively.

Synthesis of 13a, 13b, 14c, 14d, 15, 16, 17, and 23. Oligonucleotide synthesis was carried out using standard phosphoramidite chemistry. Solutions of phosphoramidites 8a, 8b, and 8e were prepared at 100 mM in acetonitrile and dried over calcium hydride granules prior to use. The coupling efficiency of the phosphoramidite 8e was strongly dependent on the drying time over calcium hydride. In the case of 8e, extended coupling times (3×10 minutes) were applied.

Modified CPGs 10c and 10d were used in Expedite columns at 1.0 µmol. Following synthesis, the support was incubated for 17 h at 55° C. in concentrated ammonium hydroxide. Volatile components were evaporated under vacuum, and the crude material was purified by C18 RP-HPLC. The purified product was confirmed by MS analysis.

B. Results

Synthesis of 3-(tert-butyldimethylsiloxy) glutaric anhydride intermediates

In the first step of the synthetic strategy, selectively protected derivatives of 3-(tert-butyldimethylsiloxy) glutaric anhydride 2, 3, 4 and 5, which can serve as intermediates for further preparations of modified solid supports or for the synthesis of new phosphoramidite reagents, were prepared (FIG. 1). This method uses commercially available and relatively inexpensive 3-(tert-butyldimethylsiloxy)glutaric anhydride 1 as the starting material that reacts easily with the primary amine $H_2N$—R'—OH containing DMT protected hydroxyl group, leading to the formation of the material 2. Compound 2 can be converted into its NHS active ester 3 representing a key intermediate material used in the subsequent transformations.

The group R' in the structure of active ester 3 can be selected from a wide variety of hydroxy amines, depending on the specific purpose of the intended modification (e.g., linker length, physicochemical or spectral properties). In the subsequent step, compound 3 can be easily converted into compound 4 by reacting with the amine $H_2N$—R". Removal of the TBDMS group from material 4 leads to the formation of the compound 5 possessing a deprotected secondary hydroxyl group.

Synthesis of Modified Phosphoramidites and Solid Supports

Figure 2:
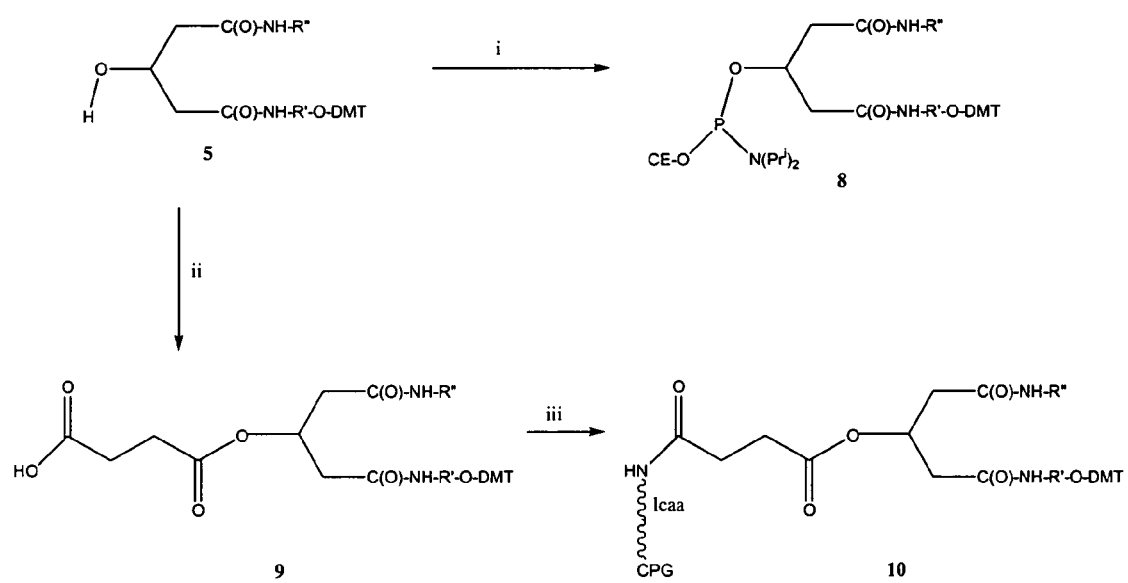
FIG. 2 shows a general scheme for the preparation of phosphoramidites and modified solid supports of some embodiments of the present invention. A general scheme for the preparation of the phosphoramidite 8 and modified solid support 10 from compound 5 is shown: (i)-CEO—P(NPr$^i_2$)$_2$/tetrazole; (ii) succinic anhydride/DMAP/base; (iii) lcaa-CPG/NHS/DCC/DMAP.

FIG. 2 illustrates the transformation of synthesized compound 5 into phosphoramidite 8 or modified solid support 10. In these experiments, $CH_2CH_2$ was selected as the R' group due to the relative ease of preparing O-DMT protected ethanoloamine. The reaction between the anhydride 1 and the O-DMT-protected ethanolamine led to the formation of an intermediate material 2, R'=$CH_2CH_2$, which was isolated by silica gel column chromatography. However, the preparation of compound 2, R'=$CH_2CH_2$, was associated with the formation of a trace amount of material that had a higher polarity than the desired reaction product. The mass spectral analysis and TLC mobility ($R_f$) of the isolated impurity were identical to those of the material formed when compound 2, R'=$CH_2CH_2$, was treated with TBAF solution (Greene, T. W., and Wuts, P. G. M. (1999) *Protective groups in organic synthesis* Wiley, New York). No detailed study addressing the conditions promoting the formation of a trace amount of the desilylated material was conducted. To overcome this minor inconvenience and to simplify the synthetic protocol, active ester 3, R'=$CH_2CH_2$ was synthesized in a one-pot procedure without isolating the corresponding intermediate material 2.

Figure 3:
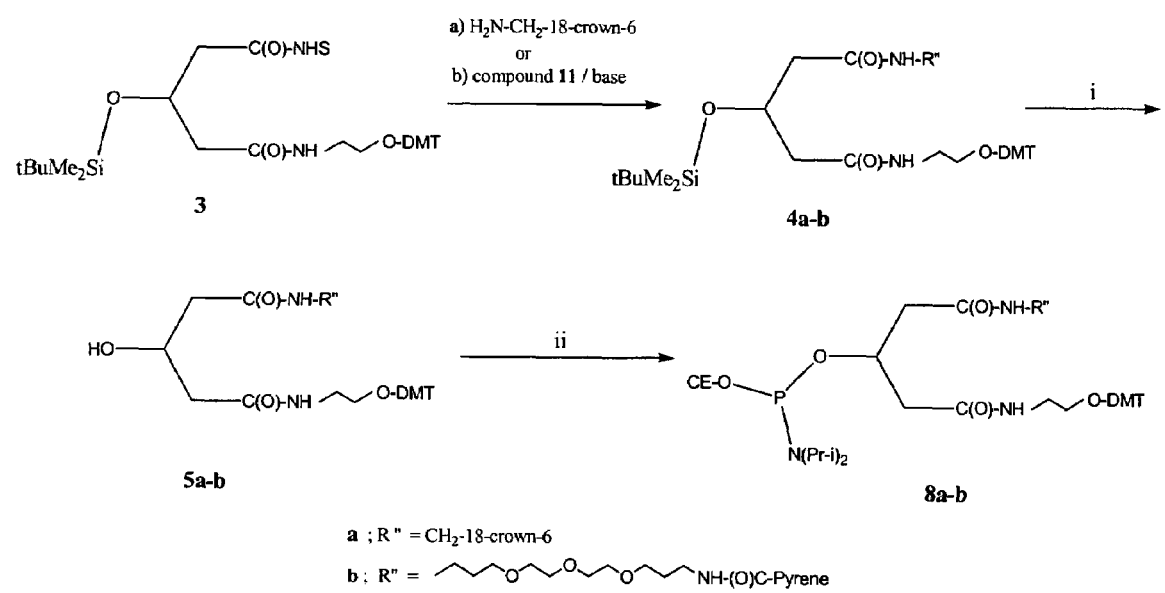
FIG. 3 shows synthesis of additional compounds and phosphoramidites of some embodiments of the present invention. Synthesis of 4a-b, compounds 5a-b and phosphoramidites 8a and 8b is shown: (i) TBAF/THF; (ii) CEO—P(NPr$^i_2$)$_2$/Tetrazole.
Figure 4:
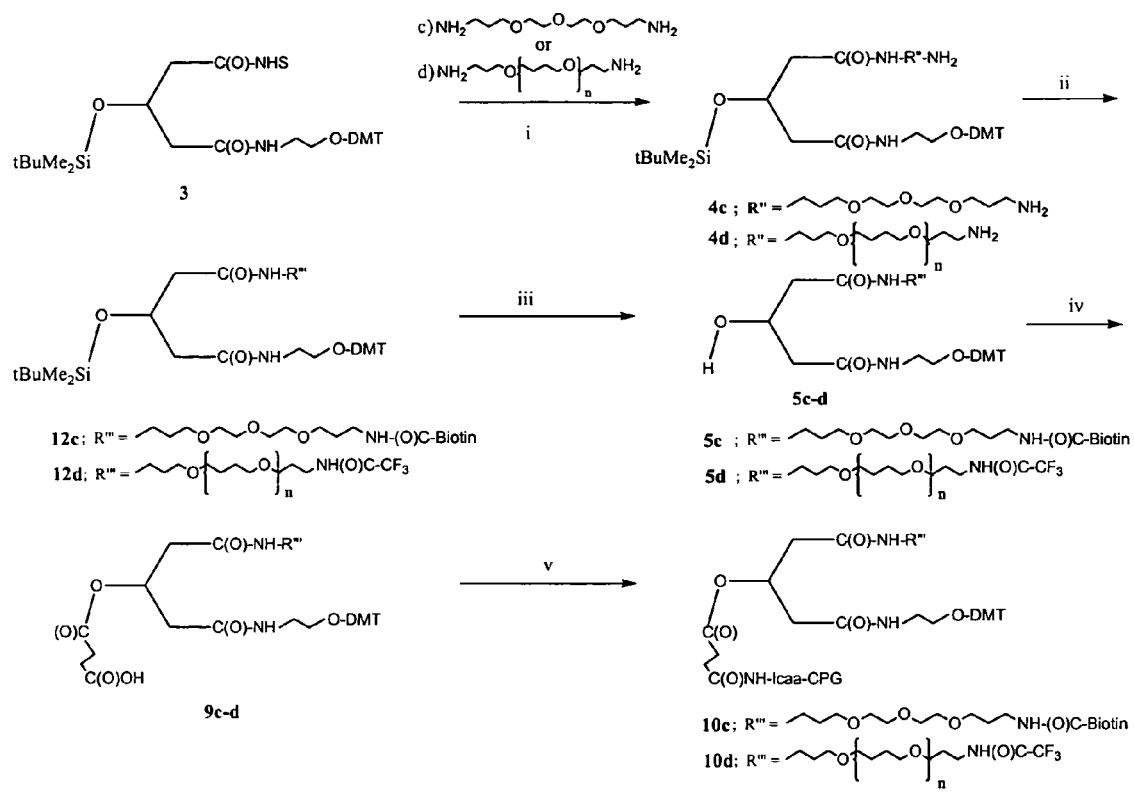
FIG. 4 shows synthesis of modified phosphoramidites and modified solid supports of some embodiments of the present invention. Synthesis of 5c and 5d and modified solid supports 10c and 10d is shown: (i) c) 4,7,10-trioxa-1,13-tridecanediamine/base or d) Polytetrahydrofuran bis-(3-aminopropyl) terminated/base; (ii) c) Biotin/HBTU/HOBT/base or d) S-Ethyl Trifluoroacetate/base; (iii) TBAF/THF; (iv) succinic anhydride/DMAP/Base; (v) lcaa-CPG/NHS/DCC/DMAP.

The relatively low polarity of material 3, R'=$CH_2CH_2$, enabled fast and efficient purification by silica gel flash chromatography using ethyl acetate or ethyl acetate/hexane as a mobile phase. Compound 3, R'=$CH_2CH_2$, was stable when stored in its crystalline form at 4° C. for six months. In addition, its preparation was easily scaled up. FIGS. 3 and 4 illustrate the synthesis of four different compounds 5a-d from the same starting material 3, (R'=$CH_2CH_2$).

Compounds 4a and 4b (FIG. 3) were synthesized correspondingly by the direct reaction of NHS ester 3, R'=$CH_2CH_2$, with commercially available 2-(aminomethyl)-18-crown-6 (Vogel et al., (2003) *Chem Commun* 1006-1007; Wu, X., and Pitsch, S. (1998) *Nucleic Acids Res* 26, 4315-4323) or with the amino derivative of the pyrene butyric acid 11 (Yamana et al., (2002); Kostenko et al., (2001) *Nucleosides Nucleotides Nucleic Acids* 20, 1859-1870). Removal of the TBDMS from synthesized compounds 4a and 4b with the THF solution of TBAF under standard reaction conditions (Greene and Wuts, supra) yielded compounds 5a and 5b with deprotected secondary hydroxyl groups. In the subsequent step, synthesized compounds 5a and 5b were converted into phosphoramidites 8a and 8b, as illustrated in FIG. 3. When used in the synthesis of 5'-modified probes 13a and 13b (FIG. 5), these phosphoramidites demonstrated full compatibility with the standard phosphoramidite protocol for automated oligonucleotide synthesis.

Incorporation of Labels into Modified Phosphoramidites and Solid Supports

The synthesis of compounds 5c and 5d (Scheme 5) required additional steps. In the first step, the active NHS ester 3, R'=$CH_2CH_2$, was reacted with an excess of the appropriate bis-amine (4,7,10-trioxa-1,13-tridecanediamine or polytetrahydrofuran-bis-(3-aminopropyl) terminated). The resulting intermediate compounds 4c and 4d, containing free primary amino groups, were isolated by silica gel chromatography.

In the next step the primary amino groups present in the isolated intermediate compounds 4c and 4d were reacted with either biotin NHS active ester producing compound 12c or S-ethyl trifluorothioacetate (Green and Wuts, supra) producing compound 12d. As with the synthesis of compounds 5a and 5b, treatment of the amino-protected intermediate materials 12c and 12d with TBAF caused the removal of the TBDMS protecting group and resulted in compounds 5c and 5d. In all cases, standard reaction conditions for the described chemical transformations were applied.

Figure 5:
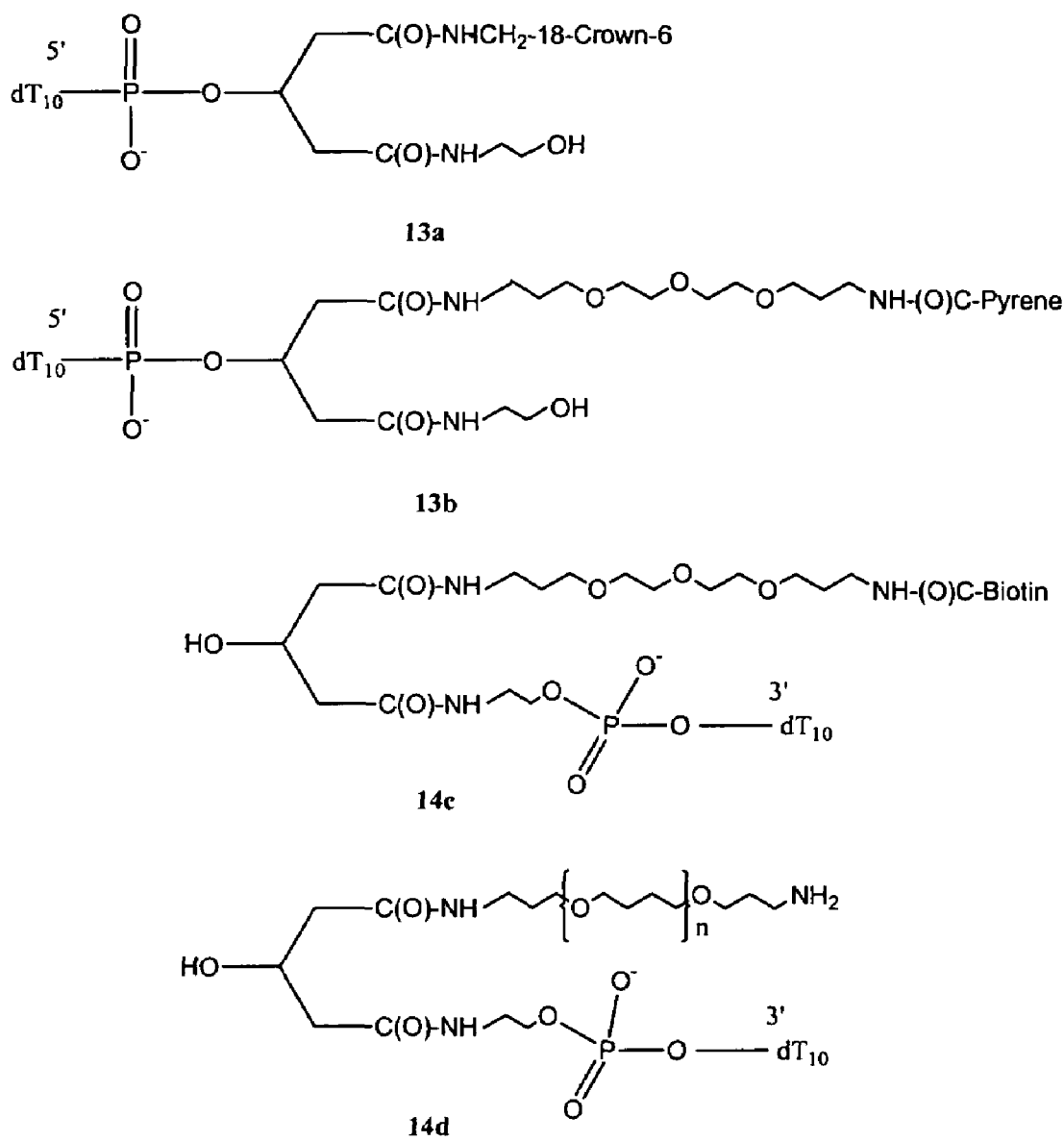
FIG. 5 shows modified nucleic acid probes of some embodiments of the present invention. 5'-modified probes 13a and 13b and 3'-modified probes 14c and 14d are shown.

Compounds 5c and 5d were used to prepare the respective solid supports, 10c and 10d (FIG. 4), which were used in the synthesis of 3'-modified DNA probes 14c and 14d, shown in FIG. 5.

Synthesis of Modified Oligonucleotide Probes

Figure 6:
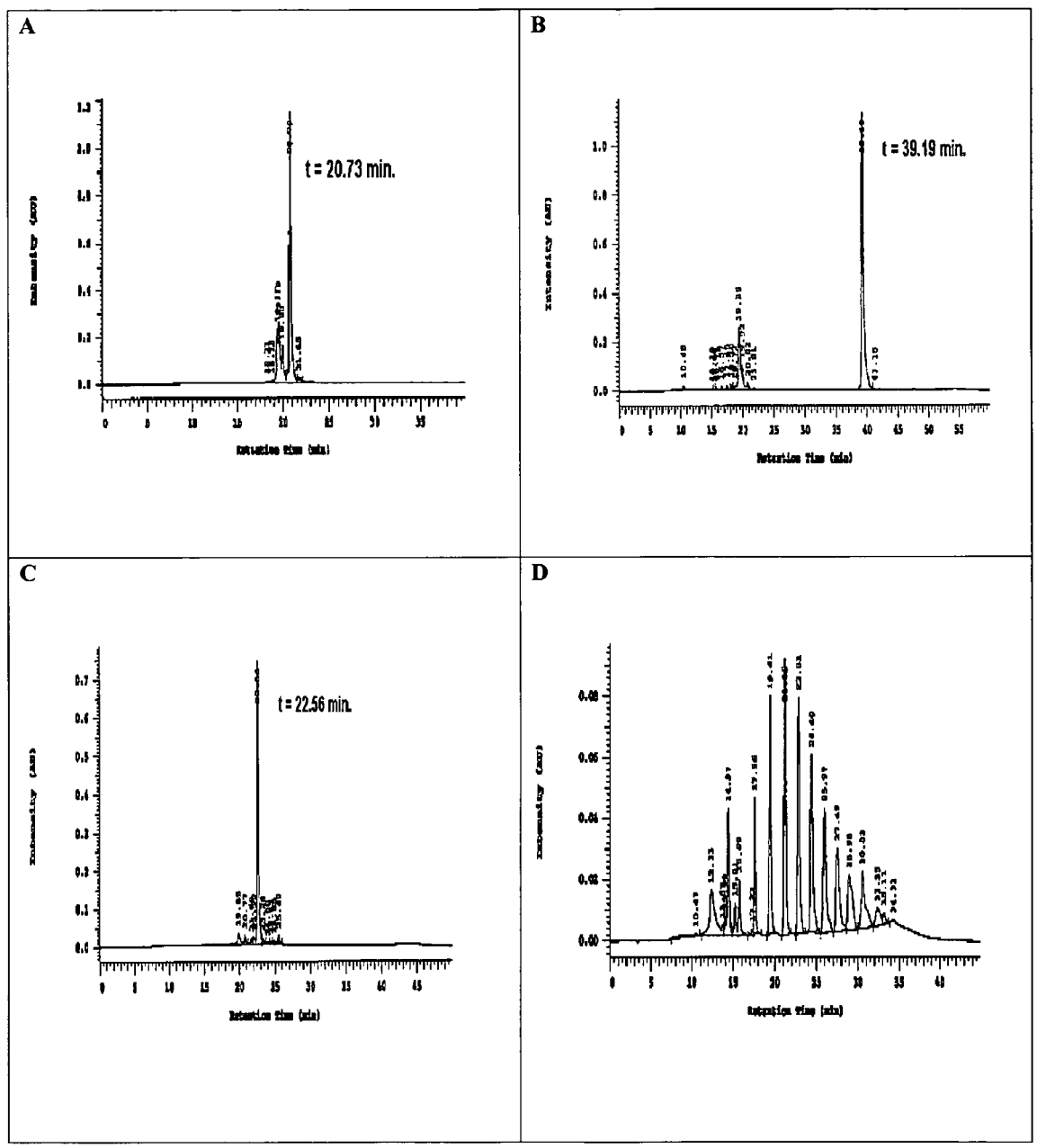
FIG. 6 shows HPLC analysis of labeled probes of some embodiments of the present invention. C18 RP HPLC analysis of the labeled probes (A) probe 13a, 1%/min acetonitrile gradient; (B) probe 13b, 1%/min acetonitrile gradient; (C) probe 14c, 1%/min acetonitrile gradient; (D) probe 14d, 2%/min acetonitrile gradient is shown.
Figure 7:
FIG. 7 shows labeled probes of some embodiments of the present invention. Compound 15 and compound 16 are shown.
Figure 7:
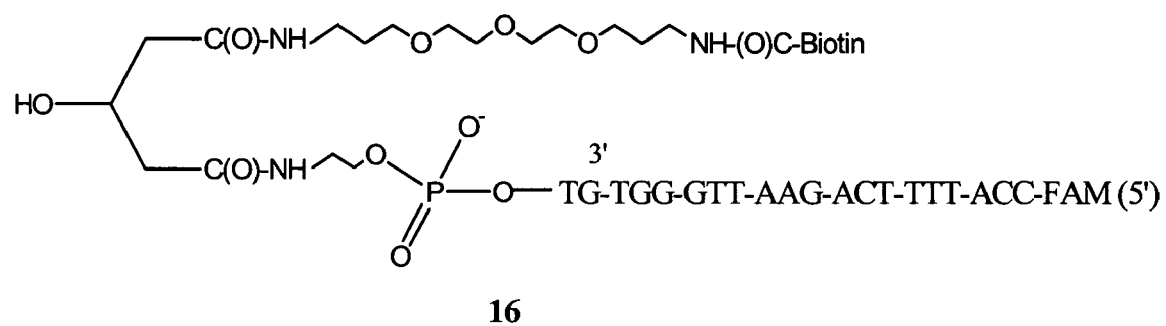

The 3'-amino modified probe 14d (R''=poly-THF—NHC(O)CF$_3$, average M$_n$ ca. 1100), in which the amino group is separated from the DNA moiety by a long polymeric linker, is illustrated in FIG. 5. In spite of strong interest in methods that introduce polymeric linkers into DNA probes or conjugates, few procedures exist for the preparation of such materials (e.g., Skrzypczynski, Z., and Wayland, S. (2003) *Bioconjug Chem* 14, 642-652. and Bonora et al., (1997) *Bioconjug Chem* 8, 793-797), probably due to difficulties associated with the synthesis and purification of selectively protected derivatives of polymeric hydroxyl amines or mono protected polymeric bis-amines. The efficiency of the synthesis of modified oligonucleotide probes using phosphoramidites 8a-b and modified supports 10c-d is illustrated in FIG. 6, where the reverse phase HPLC profiles of crude materials 13a-b and 14c-d are demonstrated. Synthesized 5' modified probes 13a-b and 3' modified probes 14c-d were isolated by RP HPLC, and their structure was confirmed by MALDI TOF analysis.

In a further attempt to test the compatibility of the synthesized reagents with the automated solid phase synthesis of chemically modified DNA probes, the synthesis of the 5'-FAM modified, mixed base DNA probe 15 was performed utilizing only commercial reagents and the 3'-biotin and 5'-FAM modified mixed base DNA probe 16 utilizing solid support 10c. These modified reagents are illustrated in FIG. 6.

Figure 8:
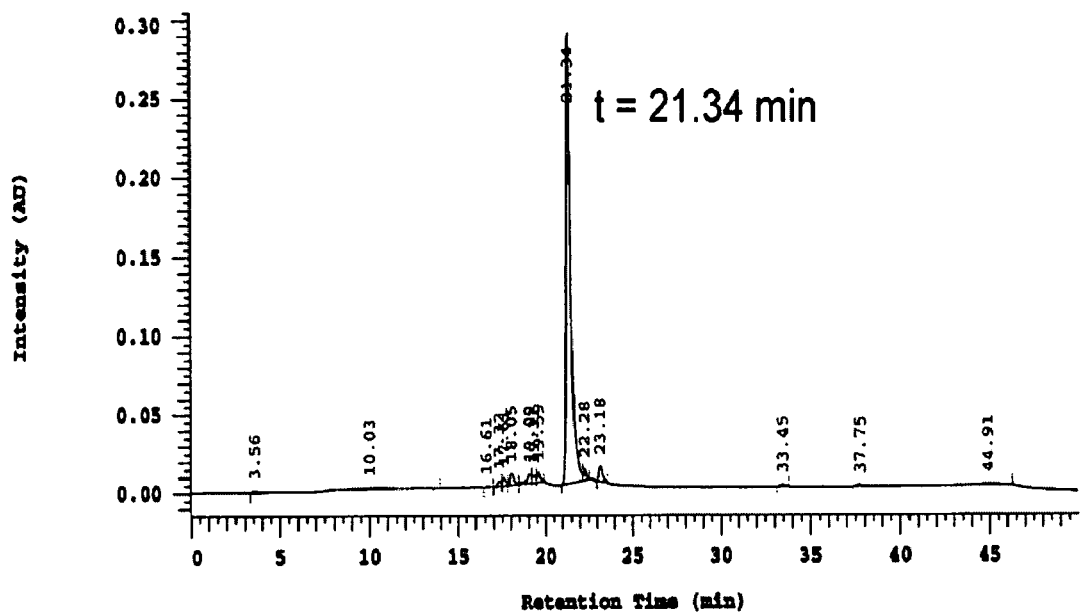
FIG. 8 shows HPLC analysis of additional labeled probes of some embodiments of the present invention. C18 RP HPLC analysis for the labeled probes (A) probe 15, 1%/min acetonitrile gradient; (B) probe 16, 1%/min acetonitrile gradient.
Figure 8:
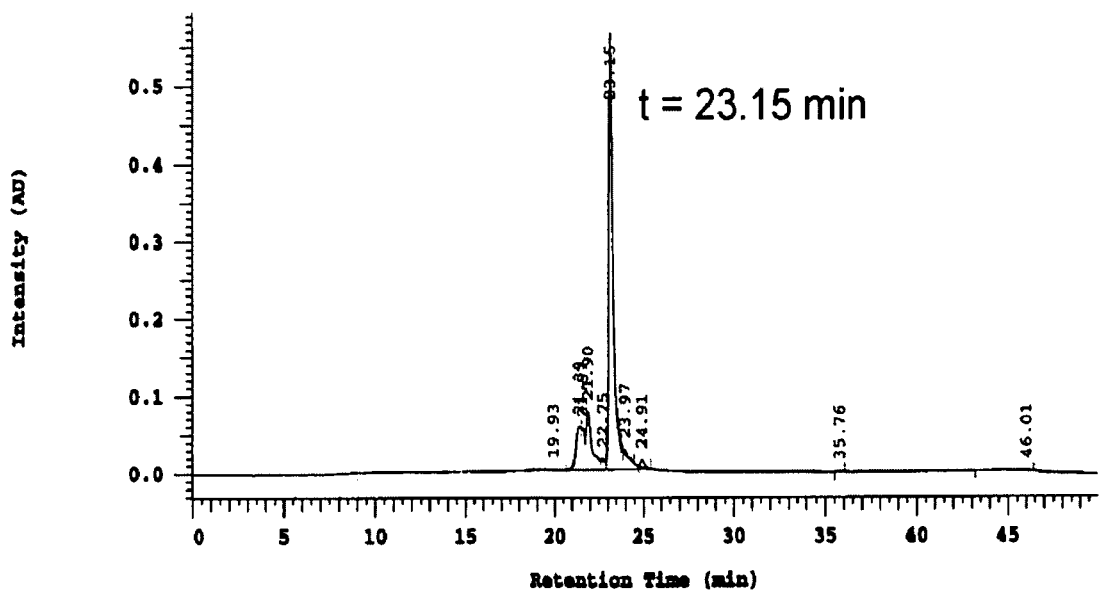

Comparison of the analytical RP HPLC profiles of the synthesized crude material 15 and the crude material 16 supports the conclusion that the synthetic performance of the biotin-modified solid support 10c is similar to that of the commercially available dT-CPG solid support, FIG. 8.

Synthesis of Oligonucleotides Comprising Internal Modifications

Figure 9:
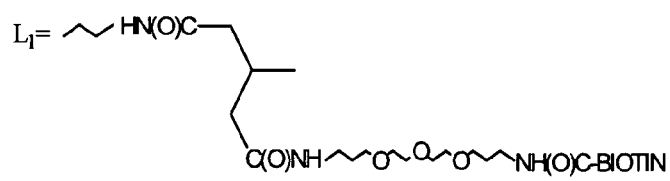
FIG. 9 shows an additional compound of some embodiments of the present invention (Compound 17).
Figure 9:
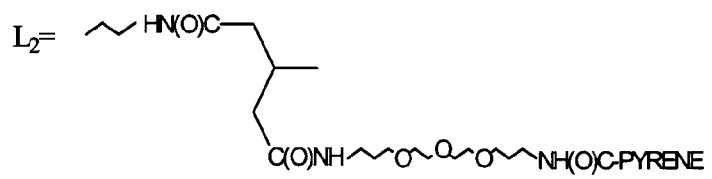
Figure 10:
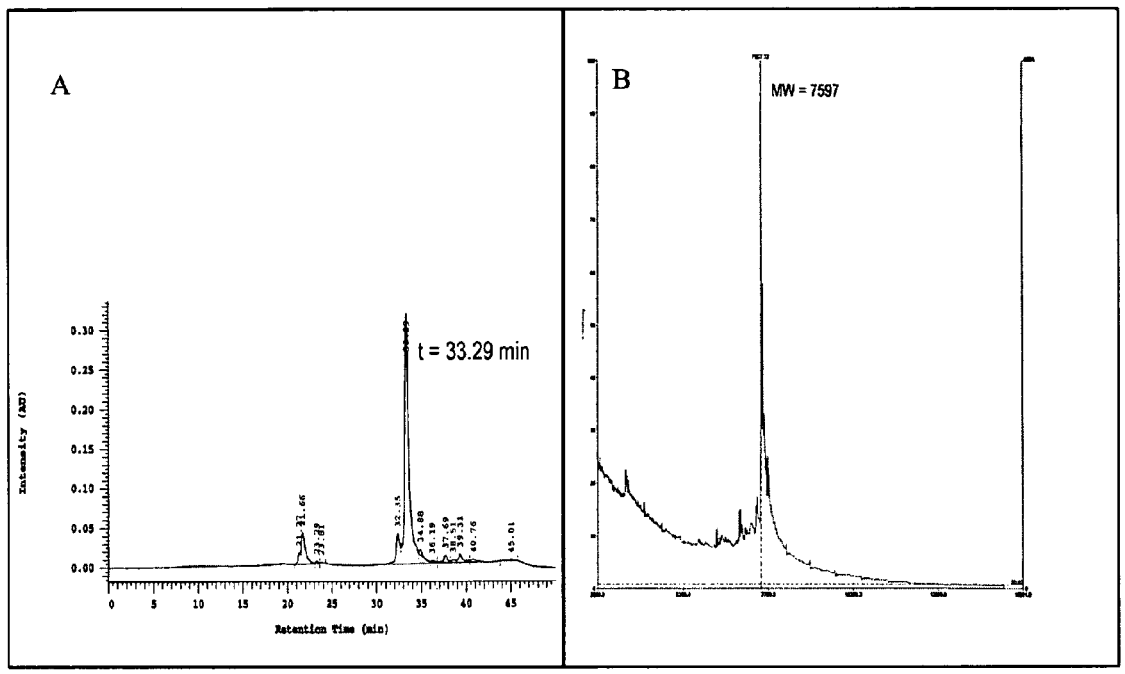
FIG. 10 shows HPLC and MALDI-TOF analysis of the labeled probe presented in FIG. 9. (A) C18 RP HPLC analysis of labeled probe 17, 1%/min acetonitrile gradient; (B) MALDI TOF analysis of labeled probe 17, calculated MW. 7600.

The applicability of the phosphoramidites 8 to the synthesis of internally modified DNA probes was additionally demonstrated by the successful synthesis of the 3' modified and internally modified DNA probe 17, which was performed using the solid support 10c and the phosphoramidite 8b, FIG. 9. The analytical RP HPLC profile of the crude material 17 along with the MALDI TOF analysis of the HPLC purified reaction product are presented in FIG. 10.

Alternative Synthesis of Modified Intermediates

Figure 11:
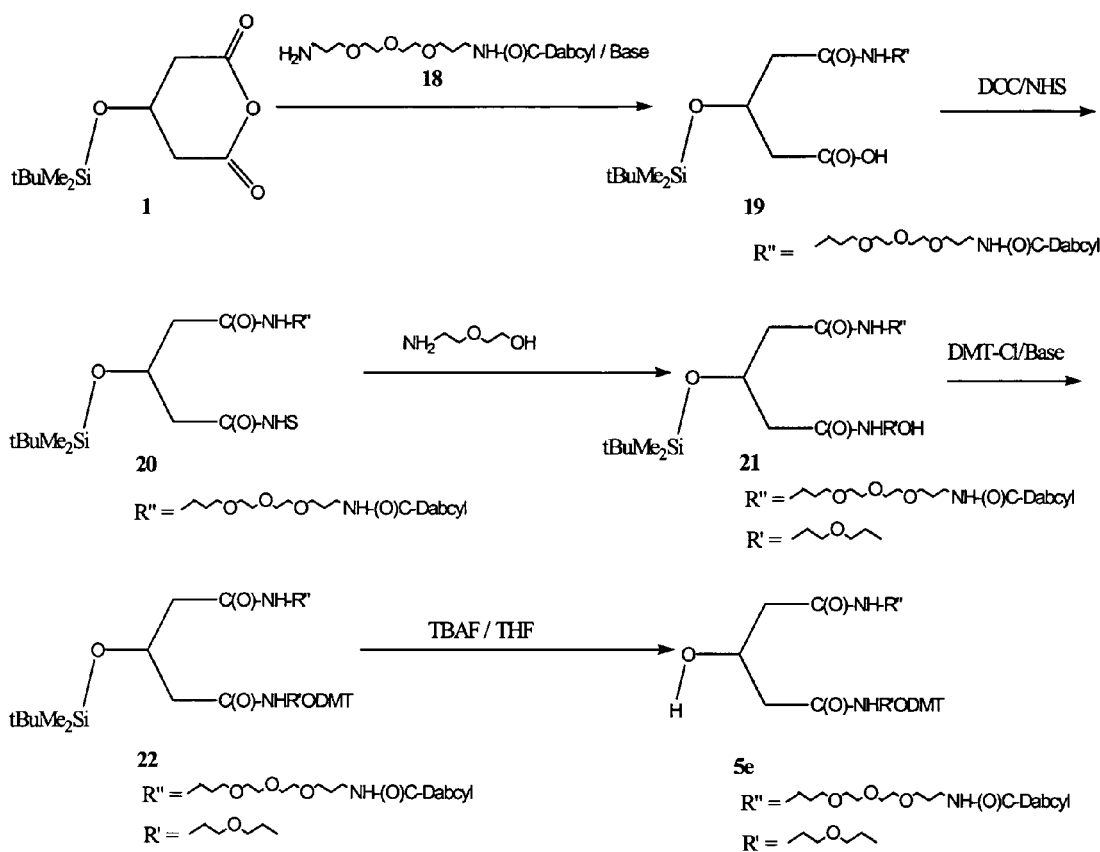
FIG. 11 shows an alternative synthesis of some exemplary compounds of the present invention. Alternate route of the synthesis of compound 5e is shown.

Alternative synthetic strategies can be used to generate compound 5 using 3-(tert-butyldimethylsiloxy)glutaric anhydride 1 as a starting material. For example, FIG. 11 illustrates that the reaction of the anhydride 1 with the desired amino derivative 18 leads to the formation of compound 19. The conversion of 19 into the NHS ester 20 and its subsequent reaction with an excess of unprotected hydroxyloamine leads to the formation compound 21 in a convenient one-pot reaction without isolation of the intermediate materials 19 and 20.

Figure 12:
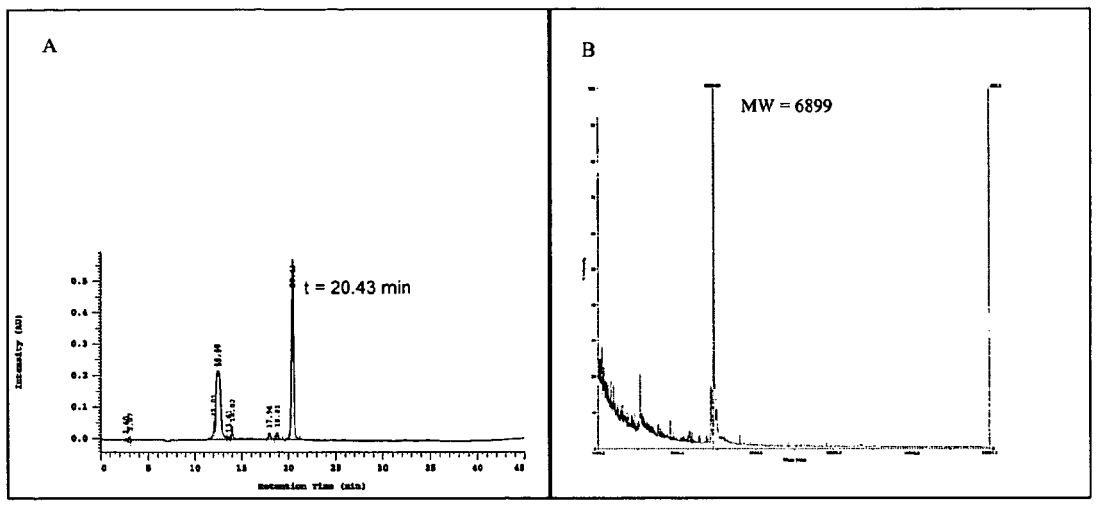
FIG. 12 shows structure, HPLC, and MALDI-TOF analysis of an exemplary purified labeled probe of the present invention. (A) C18 RP HPLC analysis of labeled probe 23, 2%/min acetonitrile gradient; (B) MALDI TOF analysis of purified labeled probe 23. calculated M.W. 6889; (C) The structure of the phosphoramidite 8e and the 5'-modifed DNA probe 23 is shown.
Figure 12:
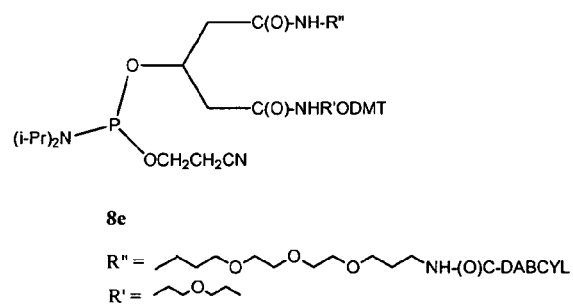
Figure 12:
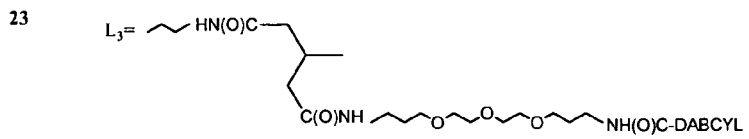

After separation by column chromatography from other components present in the reaction mixture, compound 21 was easily converted into the DMT protected derivative 22 and finally, after the removal of the TBDMS protecting group, into compound 5e. In some cases this alternate synthetic approach may offer significant synthetic advantages, particularly when the preparation of a specific O-DMT protected hydroxyloamine is synthetically difficult. Similarly, as it was observed in the synthesis of phosphoramidites 8a-b, material 5e was easily converted into the phosphoramidite 8e under standard reaction conditions. The reactivity of the phosphoramidite 8e was documented by the synthesis of the 5'-modified DNA probe 23. The structure of the phosphoramidite 8e and the material 23 are illustrated in FIG. 12. FIG. 12 includes the analytical RP HPLC profile of the crude material 23 and the MALDI TPF analysis of the purified material 23.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

What is claimed is:

1. A composition comprising:

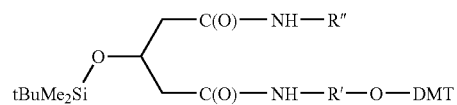

wherein R' is a polymeric linker, said polymeric linker having a structure selected from the group consisting of [CH$_2$]$_n$, and [(CH$_2$)$_a$O]$_n$, and wherein R" is selected from the group consisting of a label, an amino group, and a biological molecule, wherein said biological molecule is selected from the group consisting of proteins, lipids, carbohydrates, and nucleic acids, wherein R" optionally comprises a polymeric linker having a structure selected from the group consisting of [CH$_2$]$_n$, and [(CH$_2$)$_a$O]$_n$, wherein a is 2 or 4, and n is 1 or greater.

2. The composition of claim 1, wherein R' is CH$_2$CH$_2$.

* * * * *